(12) United States Patent
Ben-Bassat et al.

(10) Patent No.: US 7,157,256 B2
(45) Date of Patent: Jan. 2, 2007

(54) METHOD FOR PRODUCING PARA-HYDROXYSTYRENE AND OTHER MULTIFUNCTIONAL AROMATIC COMPOUNDS USING TWO-PHASE EXTRACTIVE FERMENTATION

(75) Inventors: Arie Ben-Bassat, Newark, DE (US); David J. Lowe, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 357 days.

(21) Appl. No.: 10/824,237

(22) Filed: Apr. 14, 2004

(65) Prior Publication Data

US 2004/0229326 A1    Nov. 18, 2004

Related U.S. Application Data

(60) Provisional application No. 60/545,888, filed on Feb. 19, 2004, provisional application No. 60/462,827, filed on Apr. 14, 2003.

(51) Int. Cl.
*C12P 7/22* (2006.01)
*C12P 7/40* (2006.01)
*C12P 7/42* (2006.01)

(52) U.S. Cl. .................. 435/136; 435/146; 435/156

(58) Field of Classification Search .............. 435/136, 435/146, 156
See application file for complete search history.

(56) References Cited

U.S. PATENT DOCUMENTS

| 2,053,770 | A | 9/1936 | Dreyfus |
| 4,865,973 | A | 9/1989 | Kollerup et al. |
| 6,368,837 | B1 | 4/2002 | Gatenby et al. |

FOREIGN PATENT DOCUMENTS

EP    0216221 B1    7/1994
WO    WO 01/98521 A2    12/2001

OTHER PUBLICATIONS

U.S. Appl. No. 60/383,450, filed May 23, 2002, DuPont Appl.
U.S. Appl. No. 10/138,970, filed May 3, 2002, DuPont Appl.
Jones et al., Biotechnol. Lett. Ethanol Production from Lactose by Extractive Fermentation, 15: pp. 871-876, 1993.
Daugulis et al., Continuous Fermentation of High-Strength Glucose Feeds to Ethanol, Biotechnol. Lett. 16: 637-642, 1994.
Lewis et al., A Novel Extractive Fermentation Process for Propionic Acid Production from Whey Lactose, Biotechnol. Prog. 8: 104-110, 1992.
Barton et al., Evaluation of solvents for extractive butanol fermentation with Clostridium acetobutylicum and the use of poly(propylene glycol) 1200, Appl. Microbiol. Biotechnol. 36: pp. 632-639, 1992.
Lee et al., Decarboxylation of ferulic acid to 4-vinylgualacol by Bacillus pumilus in aqueous-organic solvent two-phase systems, Enzyme Microb. Technol. 23: pp. 261-266, 1998.
Bruce et al., Solvent Selection Strategies for Extractive Biocatalysis, Biotechnol. Prog. 7: pp. 116-124, 1991.
Eiteman et al., In situ extraction versus the use of an external column in fermentation, Appl. Microbiol. Biotechnol. 30: pp. 614-618, 1989.
Playne et al., Toxicity of Organic Extraction Reagents to Anaerobic Bacteria, Biotechnol. Bioeng. 25: pp. 1251-1265, 1983.
Collins et al., Biodegradation of Phenol at High Initial Concentrations in Two-Phase Partitioning Batch and Fed-Batch Bioreactors, Biotechnol. Bioeng. 55: 155-162, 1997.
Volfova et al., Alcohol oxidase in Candida Biodinii on Methanol-Xylose Mixtures, Biotechnol. Techniques, vol. 10: pp. 643-648, 1996.

*Primary Examiner*—Herbert J. Lilling

(57) ABSTRACT

Methods are provided for the production and recovery of multifunctional aromatic compounds from a fermentation medium. Preferred multifunctional aromatic compounds include para-hydroxycinnamic acid (pHCA), cinnamic acid (CA), and para-hydroxystyrene (pHS). The multifunctional aromatic compounds may be produced in a biphasic growth medium comprising a fermentation medium having a specified volume of an extractant. The multifunctional aromatic compounds are extracted into the extractant and recovered by standard means.

15 Claims, 1 Drawing Sheet

Figure 1:
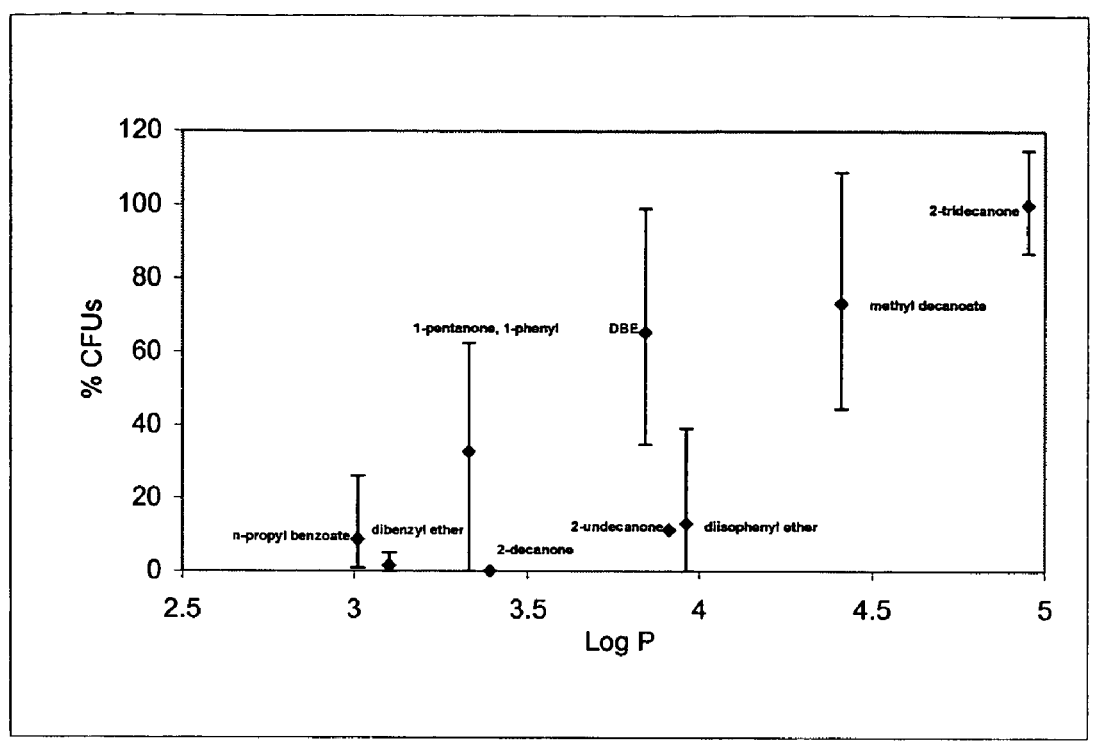

METHOD FOR PRODUCING PARA-HYDROXYSTYRENE AND OTHER MULTIFUNCTIONAL AROMATIC COMPOUNDS USING TWO-PHASE EXTRACTIVE FERMENTATION

This application claims the benefit of U.S. provisional application 60/462,827, filed Apr. 14, 2003 and 60/545,888 filed Feb. 19, 2004, the disclosures of which are incorporated in their entirety by reference.

FIELD OF THE INVENTION

The invention relates to the field of bioprocessing. More specifically, the invention relates to a method for producing para-hydroxystyrene and other multifunctional aromatic compounds by microorganisms, in which the product is removed by extraction into an immiscible organic solvent during the fermentation.

BACKGROUND OF THE INVENTION

Multifunctional aromatic compounds, which comprise an aromatic ring and two or more functional groups, have potential utility in a wide variety of industrial applications. Examples include para-hydroxycinnamic acid (pHCA), cinnamic acid (CA), and para-hydroxystyrene (pHS). These aromatic compounds have application in monomers for the production of liquid crystalline polymers, and in the production of resins, elastomers, coatings, adhesives, automotive finishes and inks.

Chemical synthetic methods for producing these aromatic compounds are known. However, these chemical methods are expensive due to the high cost of the starting materials and the extensive product purification required. Moreover, these methods generate large amounts of unwanted byproducts. Consequently, biological production methods for these aromatic compounds have been developed. For example, Gatenby et al. in U.S. Pat. No. 6,368,837 describe several methods for producing pHCA from glucose using recombinant microorganisms. A biological process for the production of pHS from a simple carbon source such as glucose is described by Ben-Bassat et al. in co pending U.S. Patent Application No. 60/383,450. Additionally, Qi et al. in co pending U.S. patent application Ser. No. 10/138,970 describe methods for producing CA and pHCA using recombinant microorganisms. However, a problem encountered with the biological production of these aromatic compounds is end-product inhibition, which limits product yield. Specifically, the rate of production of the product by the microorganism decreases as the concentration of the product increases. Additionally, the microorganism becomes inactivated by the product when a certain critical concentration is reached in the fermentation medium.

One approach to mitigate end-product inhibition is to use two-phase extractive fermentation, in which the product is extracted into an immiscible organic phase during the fermentation so that it never reaches an inhibitory or critical concentration. In this way, the microorganism can function at a high rate of production over an extended period of time.

The principle of two-phase extractive fermentation was first described by Dreyfus in U.S. Pat. No. 2,053,770. In that disclosure, the extractive fermentation of alcohol and acetone/butanol using organic solvents such as isoamyl alcohol is described. Kollerup et al. in U.S. Pat. No. 4,865,973 and European Patent No. 0216221 describe a process for the two-phase extractive fermentation of ethanol, acetone/butanol, penicillin, citric acid, and polysaccharides. In those disclosures a variety of solvents are taught, including: double bond unsaturated aliphatic alcohols having 12 or more carbon atoms; saturated branched chain aliphatic alcohols having 14 or more carbon atoms or mixtures thereof; double bond unsaturated aliphatic acids having 12 or more carbon atoms; aliphatic and aromatic mono-, di- or tri-esters having 12 or more carbon atoms, other than dibutyl phthalate; aliphatic noncyclic ketones and aliphatic aldehydes having 12 or more carbon atoms; and mixtures thereof.

There are other examples of two-phase extractive fermentation in the art. For example, see Jones et al., *Biotechnol. Lett.* 15:871–876 (1993); Daugulis et al., *Biotechnol. Lett.* 16:637–642 (1994); Lewis et al., *Biotechnol. Prog.* 8:104–110 (1992); and Barton et al., *Appl. Microbiol. Biotechnol.* 36:632–639 (1992). Lee et al. (*Enzyme Microb. Technol.* 23:261–266 (1998)) describe the production of 4-vinylguaiacol (4-hydroxy-3-methoxystyrene), a derivative of pHS, via the decarboxylation of ferulic acid by resting cells of *Bacillus pumilus* using a two-phase, biocatalytic process. Several solvents were evaluated, including chloroform, methylene chloride, ethylacetate, ethyl ether, petroleum ether, cyclohexane, and $C_5-C_8$ alkanes. Hexane was selected as the preferred solvent. All of these solvents are toxic to microorganisms and/or are hazardous, and therefore, are unsuitable for the commercial scale production of multifunctional aromatic compounds via fermentation.

As indicated by the above, although methods have been developed for two-phase extraction of fermentation products, there have been no reports of the use of extractive fermentation in the production and recovery of pHCA, CA, or pHS. This may be in part because the development of novel two-phase extractive fermentation systems is a difficult and arduous task for one skilled in the art because of the unpredictable nature of these systems. For example, the selection of the solvent is very critical and the optimal solvent must be determined for each product/microorganism combination. The solvent must meet the following requirements for use in a commercial two-phase extractive fermentation process: low solubility in water, nontoxic to the producing microorganism, large partition coefficient for the product, low partition coefficient for nutrients, high selectivity, low emulsion forming tendency, high chemical and thermal stability, nonbiodegradability, nonhazardous, and low cost (Bruce et al., *Biotechnol. Prog.* 7:116–124 (1991)). Methods for predicting the biocompatibility of organic solvents (Bruce et al., Supra) have been suggested, however those methods address only one of the parameters needed for the development of a two-phase extractive solvent system. Moreover, those methods only serve as a guide for the selection of non-toxic solvents. The actual toxicity of the solvent can only be determined by experimental testing.

Toxicity testing of the solvent system is a particular problem and solvent toxicity is difficult to predict (Eiteman et al. *Appl. Microbiol. Biotechnol.* 30:614–618 (1989)). Playne et al. (*Biotechnol. Bioeng.* 25:1251–1265 (1983))

report diisoamyl ether (diisopentyl ether), is nontoxic toward anaerobic bacteria, as determined using flask tests. Staley et al. in WO 01/98521 describe a method for extracting carboxylic acids from fermentation broth using 2-decanone. Collins et al. (*Biotechnol. Bioeng.* 55:155–162 (1997)) and *Biotechnol. Techniques* 10:643–648 (1996)) describe the biodegradation of phenol by *Pseudomonas putida* in two-phase bioreactors using 2-undecanone as solvent. In that disclosure the organic solvent was used to control delivery of a toxic substrate, not to extract the product of a fermentation. Eiteman et al., supra, describe experimental testing of 24 solvents for two-phase extractive fermentation to produce 2,3-butanediol using *Klebsiella oxytoca*.

None of the above described solvents have been reported for the extraction of multifunctional aromatic compounds such as pHCA, CA, and pHS, and clearly a need exists for fermentative extraction of these compounds.

Applicants have met the stated need by providing a method for the production of multifunctional aromatic compounds, such as pHCA, CA, and pHS, in high yield using two-phase extractive fermentation with a novel group of extractive solvents.

SUMMARY OF THE INVENTION

The present invention provides methods for the recovery of multifunctional aromatic compounds from a fermentation medium via solvent extraction. In one embodiment the invention provides a process for the recovery of a multifunctional aromatic compound from a fermentation medium comprising:

(a) providing a fermentation medium containing a multifunctional aromatic compound selected from the group consisting of cinnamic acid, para-hydroxycinnamic acid, and para-hydroxystyrene and mixtures thereof;

(b) mixing the fermentation medium of (a) with an extractant selected from the group consisting of diisopentyl ether, n-propyl benzoate, 2-undecanone, dibenzyl ether, 2-tridecanone, 2-decanone, 1-phenyl-1-pentanone, methyl decanoate, 1-undecanol, diisobutyl DBE-IB and mixtures thereof, for a time sufficient to allow extraction of the multifunctional aromatic compound into the extractant; and (c) recovering the multifunctional aromatic compound from the extractant.

In an alternate embodiment the invention provides a process for the production of a multifunctional aromatic compound comprising:

(a) providing a production host which produces a multifunctional aromatic compound selected from the group consisting of cinnamic acid, para-hydroxycinnamic acid, and para-hydroxystyrene and mixtures thereof;

(b) growing the production host in a fermentation medium wherein the production host produces a multifunctional aromatic compound into the fermentation medium to produce a conditioned medium;

(c) mixing the fermentation medium of (b) with an extractant selected from the group consisting of diisopentyl ether, n-propyl benzoate, 2-undecanone, dibenzyl ether, 2-tridecanone, 2-decanone, 1-phenyl-1-pentanone, methyl decanoate, 1-undecanol, diisobutyl DBE-IB and mixtures thereof, for a time sufficient to allow extraction of the multifunctional aromatic compound into the extractant;

(d) separating the extractant from the fermentation medium; and (e) recovering the multifunctional aromatic compound from the extractant.

In another preferred embodiment the invention provides a process for the production of a multifunctional aromatic compound comprising:

(a) providing a production host which produces a multifunctional aromatic compound selected from the group consisting of cinnamic acid, para-hydroxycinnamic acid, and para-hydroxystyrene and mixtures thereof;

(b) growing the production host of step (a) in a biphasic growth medium comprising a fermentation medium containing from about 3% to about 60% by volume of an extractant, the extractant selected from the group consisting of diisopentyl ether, n-propyl benzoate, 2-undecanone, dibenzyl ether, 2-tridecanone, 2-decanone, 1-phenyl-1-pentanone, methyl decanoate, 1-undecanol, diisobutyl DBE-IB and mixtures thereof; for a time sufficient to allow extraction of the multifunctional aromatic compound into the extractant;

(c) separating the extractant from the fermentation medium; and (d) recovering the multifunctional aromatic compound from the extractant.

BRIEF DESCRIPTION OF THE FIGURES, BIOLOGICAL DEPOSIT AND SEQUENCE DESCRIPTIONS

The invention can be more fully understood from the following detailed description, figure, and the accompanying sequence descriptions, which form a part of this application.

FIG. 1 is a graph of the growth of *E. coli* in the presence of various organic solvents plotted versus the log P value of the solvent.

Applicants made the following biological deposit under the terms of the Budapest Treaty on the International Recognition of the Deposit of Microorganisms for the Purposes of Patent Procedure:

| Depositor Identification Reference | International Depository Designation | Date of Deposit |
|---|---|---|
| *E. coli* BNT511, tyrosine overproducing strain | ATCC: PTA-4314 | May 9, 2002 |

The following sequences conform with 37 C.F.R. 1.821–1.825 ("Requirements for Patent Applications Containing Nucleotide Sequences and/or Amino Acid Sequence Disclosures—the Sequence Rules") and are consistent with World Intellectual Property Organization (WIPO) Standard ST.25 (1998) and the sequence listing requirements of the EPO and PCT (Rules 5.2 and 49.5(a-bis), and Section 208 and Annex C of the Administrative Instructions).

SEQ ID NO:1 is the nucleotide sequence of the para-hydroxycinnamic acid decarboxylase gene (pdc1) from *Lactobacillus plantarum*.

SEQ ID NOs:2 and 3 are nucleotide sequences of the primers used to amplify pdc1, as described in Example 3.

SEQ ID NO:4 is the nucleotide sequence of the phenylalanine ammonia lyase (pal gene from *Rhodotorula glutinis*.

SEQ ID NOs:5 and 6 are nucleotide sequences of the primers used to amplify pal from *Rhodotorula glutinis*, as describe in Example 3.

DETAILED DESCRIPTION OF THE INVENTION

The invention provides a method for the production and recovery of multifunctional aromatic compounds of the invention by fermentation. The method results in a higher rate of production of multifunctional aromatic compound due to a decreased exposure of the product to the production cells. The methods are useful as the multifunctional aromatic compounds of the invention (para-hydroxycinnamic acid (pHCA), cinnamic acid (CA), and para-hydroxystyrene (pHS)) have application as monomers for the production of liquid crystalline polymers, and in the production of resins, elastomers, coatings, adhesives, automotive finishes and inks.

The following definitions are used herein and should be referred to for interpretation of the claims and the specification.

"CA" is the abbreviation used for cinnamic acid.

"pHCA" is the abbreviation used for para-hydroxycinnamic acid.

"pHS" is the abbreviation used for para-hydroxystyrene.

"TAL" is the abbreviation used for tyrosine ammonia lyase.

"PAL" is the abbreviation used for phenylalanine ammonia lyase.

"PAH" is the abbreviation used for phenylalanine hydroxylase.

"DBE" is the abbreviation used for diisobutyl DBE-IB, a product of E. I. Du Pont de Nemours and Co. (Wilmington, Del.). This product consists of a mixture of diisobutyl succinate (20–30 wt %, CAS No. 925-06-4), diisobutyl glutarate (55–70 wt %, CAS No. 71195-64-7), diisobutyl adipate (10–20 wt %, CAS No. 141-04-8), and traces of isobutanol (less than 0.25 wt %, CAS No. 78-83-1) and water (less than 0.15 wt %).

The term "TAL activity" refers to the ability of a protein to catalyze the direct conversion of tyrosine to pHCA.

The term "PAL activity" refers to the ability of a protein to catalyze the conversion of phenylalanine to cinnamic acid.

"pal" represents a gene that encodes an enzyme with PAL activity.

"tal" represents a gene that encodes an enzyme with TAL activity.

"pdc" represents a gene that encodes an enzyme with pHCA decarboxylase activity.

"pdc1" represents the gene that encodes an enzyme with pHCA decarboxylase activity from *Lactobacillus plantarum*.

The term "PAL/TAL activity" or "PALITAL enzyme" refers to a protein, which contains both PAL and TAL activity. Such protein has at least some specificity for both tyrosine and phenylalanine as an enzymatic substrate.

The term "P-450/P-450 reductase system" refers to a protein system responsible for the catalytic conversion of cinnamic acid to pHCA. The P-450/P-450 reductase system is one of several enzymes or enzyme systems known in the art that performs a cinnamate 4-hydroxylase function. As used herein the term "cinnamate 4-hydroxylase" will refer to the general enzymatic activity that results in the conversion of cinnamic acid to pHCA, whereas the term "P-450/P-450 reductase system" will refer to a specific binary protein system that has cinnamate 4-hydroxylase activity.

The "log P value" of a solvent refers to the logarithm of the solvent's partition coefficient in a standard octanol:water mixture. The log P value provides a quantitative measure of the polarity of the solvent.

The term "fermentable carbon substrate" refers to a carbon source capable of being metabolized by host organisms of the present invention and particularly carbon sources selected from the group consisting of monosaccharides, oligosaccharides, polysaccharides, one-carbon substrates and/or mixtures thereof.

The terms "growth medium", "fermentation medium" and "medium" are herein used interchangeably to refer to an aqueous solution containing nutrients for culturing microorganisms. The growth medium may additionally contain the microorganism, the product produced by the microorganism, metabolic intermediates, and other components such as salts, vitamins, amino acids, cofactors, and antibiotics.

The term "biphasic growth medium" refers to a medium comprising a fermentation medium having a suitable amount of a water immiscible extractant.

The term "extractant" refers to a solvent into which a multifunctional aromatic compound may be dissolved. Typical extractants of the invention are water-immiscible organic solvents.

"Nucleic acid" refers to a molecule, which can be single stranded or double stranded, composed of monomers (nucleotides) containing a sugar, phosphate and either a purine or pyrimidine. In bacteria, lower eukaryotes, and in higher animals and plants, "deoxyribonucleic acid" (DNA) refers to the genetic material while "ribonucleic acid" (RNA) is involved in the translation of the information from DNA into proteins.

"Gene" refers to a nucleic acid fragment that effects the production of a specific protein, including regulatory sequences preceding (5" non-coding sequences) and following (3" non-coding sequences) the coding sequence.

"Transformation" refers to the transfer of a nucleic acid fragment into the genome of a host organism, resulting in genetically stable inheritance. Host organisms containing the transformed nucleic acid fragments are referred to as "transgenic" or "recombinant" or "transformed" organisms.

The term "expression" as used herein is intended to mean the transcription and translation to gene product from a gene coding for the sequence of the gene product. In the expression, a DNA chain coding for the sequence of gene product is first transcribed to a complementary RNA which is often a messenger RNA and, then, the thus transcribed messenger RNA is translated into the above-mentioned gene product if the gene product is a protein.

"Overproducing strain" refers to a recombinant microorganism that produces a gene product at a level that exceeds the level of production in normal or non-transformed microorganisms.

The term "production host" refers to a microorganism having the ability to produce a multifunctional aromatic compound of the invention. As defined herein the production host may be a wildtype or recombinant variety.

The term "multifunctional aromatic compound" refers to organic compounds comprising an aromatic ring and two or more functional groups such as hydroxyl, vinyl, and carboxylic acid. The preferred multifunctional aromatic compounds of the invention include but are not limited to cinnamic acid (CA), para-hydroxycinnamic acid (pHCA), and para-hydroxystyrene (pHS).

The instant invention comprises a method for producing multifunctional aromatic compounds using two-phase extractive fermentation, in which a substrate is fermented in an aqueous medium by means of a microorganism and the resulting product is removed from the medium by extraction into an immiscible organic solvent during the fermentation.

Multifunctional Aromatic Compounds

The multifunctional aromatic compounds of the instant invention include, but are not limited to, cinnamic acid (CA), para-hydroxycinnamic acid (pHCA), and para-hydroxystyrene (pHS) and mixtures thereof. These aromatic compounds may be prepared by transformed prokaryotic systems, using standard recombinant DNA techniques. These recombinant DNA techniques are described by Sambrook, J., Fritsch, E. F. and Maniatis, T. *Molecular Cloning: A Laboratory Manual*, Second Edition, Cold Spring Harbor Laboratory Press, Cold Spring Harbor (1989), incorporated herein by reference. Suitable recombinant host cells include, but are not limited to *Escherichia, Methylosinus, Methylomonas, Pseudomonas, Streptomyces, Corynebacterium,* and *Rhodobacter*. These bacteria, particularly the Gram-negative organisms, are known to be tolerant of organic solvents (Inoue et al., *J. Ferment. Bioeng.* 71:194–196 (1991)). The preferred host cells of the instant invention are *Escherichia coli* and *Pseudomonas putida*. The most preferred host cells of the instant invention are mutant strains of these bacteria that overproduce either phenylalanine or tyrosine. Tyrosine overproducing strains are preferred when the production of pHS is carried out via a pathway that involves tyrosine, while phenylalanine overproducing strains are preferred when pHS is produced via a pathway that involves phenylalanine, as described infra. Tyrosine overproducing strains of *Escherichia* and *Pseudomonas*, as well as other bacteria, are known in the art (Maiti et al., *Antibiotic Bulletin* 37:51–65 (1995)). An example of an *Escherichia* tyrosine overproducing strain that may be used is *E. coli* TY1, available from OmniGene Bioproducts, Inc. Cambridge, Mass. Phenylalanine overproducing strains of *Escherichia* and *Pseudomonas*, as well as other bacteria, are also known in the art (Maiti et al, supra and Bongaertes et al., *Metabolic Engineering* 3:289–300 (2001)). An example of a phenylalanine overproducing strain that may be used is *E. coli* NST 74, available as strain ATCC No. 31884 from the American Type Culture Collection, Manassas, Va. For example, pHCA and CA may be produced as described by Qi et al. in U.S. Patent Application Publication No. 2003-007925, incorporated herein by reference. According to that disclosure, CA may be produced using a recombinant microorganism engineered to express at least one gene encoding a phenylalanine ammonia lyase (PAL) activity. This transformed microorganism metabolizes a fermentable carbon source, such as glucose, to phenylalanine, which is converted to CA by the PAL enzyme. That disclosure also teaches that pHCA may be produced using a recombinant microorganism engineered to express at least one gene encoding a phenylalanine hydroxylase (PAH) activity and at least one gene encoding a tyrosine ammonia lyase (TAL) activity. This transformed microorganism metabolizes a fermentable carbon source, such as glucose, to phenylalanine, which is converted to tyrosine by PAH. The tyrosine produced is converted to pHCA by the TAL enzyme. Any suitable enzyme possessing a TAL activity may be used. For example, an enzyme having both PAL and TAL (PAL/TAL) activity may be used. TAL enzymes, produced through mutagenesis of wild-type yeast PAL enzymes to have enhanced TAL activity, may also be used, as described by Gatenby et al. in U.S. Pat. No. 6,368,837. Alternatively, an inducible TAL enzyme from the yeast *Trichosporon cutaneum*, as described by Breinig et al. (U.S. Patent Application Publication No. 2004-002335) or a bacterial TAL enzyme such as that described by Kyndt et al. (*FEBS Lett.* 512: 240–244 (2002)) or by Huang et al. (U.S. Patent Application Publication No. 2004-009795) may be used.

Para-hydroxycinnamic acid may also be produced by any one of the methods disclosed by Gatenby et al. supra, incorporated herein by reference. For example, pHCA may be produced using a recombinant microorganism engineered to express a gene encoding a yeast PAL activity and genes encoding a plant P-450/P-450 reductase system. This transformed microorganism metabolizes a fermentable carbon source, such as glucose, to phenylalanine, which is converted to CA by the PAL enzyme. CA is subsequently converted to pHCA by the action of the P-450/P-450 reductase system. Alternatively, pHCA may be produced using a recombinant microorganism expressing a gene encoding a TAL activity. The TAL enzyme converts tyrosine directly to pHCA. Any suitable TAL enzyme may be used, as described supra.

Para-hydroxystyrene may be produced as described by Ben-Bassat et al. in U.S. Patent Application Publication No. 2004-001860, incorporated herein by reference. In that disclosure, a biological method for producing pHS from a fermentable carbon source, such as glucose, is described. The transformed microorganism expresses at least one gene encoding a TAL activity and at least one gene encoding a pHCA decarboxylase activity. The TAL enzyme converts tyrosine into pHCA, which is subsequently converted into pHS by the pHCA decarboxylase enzyme. Any suitable TAL enzyme described above may be used. In the preferred embodiment of the instant invention, pHS is produced by fermentation using a recombinant strain of *Escherichia coli* or *Pseudomonas putida*.

Extractants

The extractants of the instant invention are water-immiscible organic solvents. The solvents were discovered to meet the criteria for an ideal solvent for a commercial two-phase extractive fermentation for the production of multifunctional aromatic compounds. Specifically, these solvents were determined to be nontoxic to the preferred host cells, *Escherichia coli* and *Pseudomonas putida*, to be substantially immiscible with the fermentation medium, to have a high partition coefficient for the extraction of pHS and other multifunctional aromatic compounds, to have a low partition coefficient for the extraction of nutrients, to have a low tendency to form emulsions with the fermentation medium, to be low cost and nonhazardous. The preferred solvents of the instant invention include: diisopentyl ether (CAS No. 544-014), n-propyl benzoate (CAS No. 2315-68-6), 2-undecanone (CAS No. 112-12-9), dibenzyl ether (CAS No. 103-50-4), 2-tridecanone (CAS No. 593-08-8), 2-decanone (CAS No. 693-54-9), 1-phenyl-1-pentanone (CAS No. 1009-14-9), methyl decanoate (CAS No. 11042-9), 1-undecanol (CAS No. 11242-5), and DBE. The most preferred solvents of the instant invention are 2-undecanone, DBE, 2-tridecanone and methyl decanoate. Before use in a fermentation, these solvents should be tested using shake-flask studies, as described in Example 2, infra, or agar plate studies, as described in Example 8, infra, to determine if they contain impurities that inhibit microbial growth. This was a problem observed with the solvent 2-undecanone. Specifically, some lots of 2-undecanone were found to be toxic to *E. coli* due to impurities.

In some circumstances it may be advantageous to use a mixture of the preferred solvents. For example, solvent mixtures may be used to increase the partition coefficient of the product. Additionally, solvent mixtures may be used to adjust and optimize physical characteristics of the solvent, such as the density, boiling point, and viscosity.

Under some conditions, the solvents of the instant invention, particularly DBE, may form a stable emulsion with the fermentation medium. The stability of the emulsion formed is determined by the mode of fermentation used, the agitation and aeration rates, pH, temperature, the solvent, and the composition of the fermentation medium, especially the presence of colloidal insoluble solids, proteins, surface active agents, polymers, the amount of cells, and the presence of cell lysis material. The formation of a stable emulsion complicates the separation of the fermentation medium from the organic extractant. The ease of separation of the two phases and the time required for the separation depends on the operational stability of the emulsion. If a stable emulsion is formed, it can be destabilized using methods known in the art (see for example, Mathys et al. *J. Chem. Technol. Biotechnol.* 71:326–334 (1998), Schmid et al. *Enzyme and Microbial Technology* 22:487–493 (1998), Breen et al. *Surfactant Science Series* 61:237–285 (1996), and Isaacs et al. *Emulsions: Fundamentals and Applications in the Petroleum Industry,* Advances in Chemistry Series 231, L. L. Schramm, ed., American Chemical Society, Washington, D.C., pp 51–77 (1992)). For example, to minimize stable emulsion formation, the rate of agitation and aeration in the fermentor may be reduced. In addition, the pH and temperature of the fermentation medium may be adjusted to minimize the stability of the emulsion. The optimum conditions may be determined by routine experimentation. Moreover, the amount of insolubles and polymers in the fermentation medium may be minimized by design of the medium or by filtration. The addition of surface-active agents may stabilize or destabilize the emulsion depending on the concentration used. The amount of surface-active agent required to destabilize the emulsion may be determined by routine experimentation. Emulsion formation may also be minimized by reducing the contact time between the fermentation medium and the extractant. This may be accomplished by using the external extractive fermentation mode described infra. The formation of emulsions may further be mitigated by separating the cells from the fermentation medium before contacting with the extractant in the external mode.

Methods for Producing Multifunctional Aromatic Compounds and Derivatives Thereof To produce the multifunctional aromatic compound of interest, the microorganism to be used is cultured in a fermentor in a suitable growth medium. Any suitable fermentor may be used including a stirred tank fermentor, an airlift fermentor, a bubble fermentor, or any combination thereof. Materials and methods for the maintenance and growth of microbial cultures are well known to those in the art of microbiology or fermentation science (See for example, Bailey et al., *Biochemical Engineering Fundamentals*, second edition, McGraw Hill, New York, 1986). Consideration must be given to appropriate growth medium, pH, temperature, and requirements for aerobic, microaerobic, or anaerobic conditions, depending on the specific requirements of the microorganism, the fermentation, and the process. The growth medium used is not critical, but it must support growth of the microorganism used and promote the enzymatic pathway necessary to produce the desired product. A conventional growth medium may be used, including, but not limited to complex media containing organic nitrogen sources such as yeast extract or peptone and a fermentable carbon source, minimal media, and defined media. Suitable fermentable carbon sources include, but are not limited to monosaccharides, such as glucose or fructose, disaccharides, such as lactose or sucrose, oligosaccharides and polysaccharides, such as starch or cellulose, one-carbon substrates and/or mixtures thereof. In addition to the appropriate carbon source, the growth medium may contain a suitable nitrogen source, such as an ammonium salt, yeast extract or peptone, minerals, salts, cofactors, buffers and other components, known to those skilled in the art (Bailey et al. supra).

Suitable conditions for the extractive fermentation depend on the particular microorganism used and the product produced. Typical fermentation conditions are as follows. A suitable temperature for the fermentation ranges from about 20° C. to about 80° C. The appropriate pH of the fermentation medium is from about 3.0 to about 9.0. For the production of acidic compounds, such as CA and pHCA, a lower pH is preferred because the form of the product extracted into the organic phase is the unionized acid. Therefore, for acidic products the preferred pH range is from about 3.0 to about 6.0, depending on the ionization constant ($K_a$) of the product and the growth of the microorganism at low pH. Suitable ranges for the pressure, the stir rate, and air-flow are 0.1 to 4.0 bar, 0 to 1500 rpm and 0 to 20 volume air per volume broth per min (VVM), respectively.

The solvent is typically added to the fermentation broth at the beginning of the fermentation. The volume of the organic solvent to be used depends on a number of factors, including the volume of the fermentation broth, the size of the fermentor, the partition coefficient of the solvent for the product, and the fermentation mode chosen, as described infra. Typically the volume of the organic solvent is between about 3% to about 60% of the fermentor working volume.

In a preferred embodiment of the invention, the two-phase extractive fermentation process is carried out in a continuous mode in a stirred tank fermentor. In this mode, a biphasic mixture consisting of the fermentation medium and the solvent containing the extracted product is removed from the fermentor. The two phases are separated by means known in the art including, but not limited to, a gravity settler, a centrifuge and a hydrocyclone. An example of a gravity separator is described by Kollerup et al. in U.S. Pat. No. 4,865,973, incorporated herein by reference. The use of centrifuges and hydrocyclones is well known in the art of industrial processing (See for example, *Ullmann's Encyclopedia of Industrial Chemistry*, Fifth Edition, Elvers et al. Eds., VCH Publishers, New York, Vol. B2, Chapter 11, 1988). After separation, the fermentation medium is recycled to the fermentor and the solvent is treated to recover the product by means described infra. The solvent may then be recycled back into the fermentor for the further extraction of the product. Alternatively, fresh solvent may be continuously added to the fermentor to replace the removed solvent. This continuous mode of operation offers several advantages. Because the product is continually removed from the reactor, a smaller volume of organic solvent is required, thus enabling a larger volume of the fermentation broth to be used. This results in higher production yields. In this mode, the volume of the organic solvent is between about 3% to about 30%, preferably between about 3% to about 20%, most preferably between about 3% to about 10% of the fermentor working volume. It is preferred to use the smallest amount of solvent in the fermentor as possible to maximize the volume of the aqueous phase, and therefore, the amount of cells in the fermentor. Moreover, the process may be operated in an entirely continuous mode in which the solvent is continuously recycled between the fermentor and a separation apparatus and the fermentation medium is continuously removed from the fermentor and replenished with fresh medium. In this entirely continuous mode, the product is not allowed to reach the critical toxic concentration and fresh nutrients are continuously provided so that the fermentation may be carried out for long periods of time. The apparatus that may be used to carryout these modes of two-phase extractive fermentations are well known in the art. Examples are described by Kollerup et al. in U.S. Pat. No. 4,865,973, incorporated herein by reference.

In another embodiment of the instant invention, a batch-wise fermentation mode is used. Batch fermentation, which is well known in the art, is a closed system in which the composition of the medium is set at the beginning of the fermentation and is not subjected to artificial alterations during the process. In this mode, a volume of organic solvent is added to the fermentor at the beginning of the fermentation and the solvent is not removed during the process. Although this mode is simpler than the continuous or the entirely continuous modes described supra, it requires a larger volume of organic solvent to minimize the concentration of the inhibitory product in the growth medium. Consequently, the volume of the growth medium must be less and the amount of product produced is less than that obtained using the continuous mode. In the batchwise mode, the volume of the organic solvent is between about 20% to about 60%, preferably between about 30% to about 60% of the fermentor working volume. It is preferred to use the smallest volume of solvent in the fermentor as possible, for the reason described supra.

In another embodiment of the instant invention, a fed-batch fermentation mode is used. Fed-batch fermentation is a variation of the standard batch system, in which the nutrients, for example glucose, are added in increments during the fermentation. The amount and the rate of addition of the nutrient may be determined by routine experimentation. For example, the concentration of critical nutrients in the fermentation broth may be monitored during the fermentation. Alternatively, more easily measured factors such as pH, dissolved oxygen, and the partial pressure of waste gases, such as carbon dioxide, may be monitored. From these measured parameters, the rate of nutrient addition may be determined. The amount of organic solvent used in this mode is the same as that used in the batch-wise mode, described supra.

In yet another embodiment of the instant invention, the extraction of the product may be done downstream of the fermentor, rather than in situ. In this external mode, a batch-wise fermentation or a fed-batch fermentation is used and the liquid—liquid extraction of the product is carried out on the fermentation medium, removed from the fermentor. The amount of organic solvent used in this mode is between about 20% to about 60%, preferably between about 30% to about 60% of the fermentor working volume. The fermentation medium may be removed from the fermentor continuously or periodically, and the extraction of the product by the organic solvent may be done with or without the removal of the cells from the fermentation medium. The cells may be removed from the fermentation medium by means known in the art including, but not limited to, filtration or centrifugation. After separation of the fermentation medium from the solvent by means described supra, the fermentation medium may be recycled into the fermentor, discarded, or treated for the removal of any remaining product. Similarly, the isolated cells may also be recycled into the fermentor. After treatment to recover the product, the solvent may be recycled for use in the extraction process. Alternatively, fresh solvent may be used. In this mode the solvent is not present in the fermentor, so the toxicity of the solvent is much less of a problem. If the cells are separated from the fermentation medium before contacting with the solvent, the problem of solvent toxicity is further reduced. Furthermore, using this external mode there is less chance of forming an emulsion and evaporation of the solvent is minimized, alleviating environmental concerns.

After the product is extracted from the fermentation medium into the solvent, it may be recovered from the solvent by methods well known in the art, including but not limited to distillation, adsorption by resins or separation by molecular sieves. The preferred method of product recovery from the organic solvent is distillation.

Additionally, the product may be chemically derivatized in the extractant before it is recovered. Any suitable chemical derivatization method known in the art may be used. For example, CA derivatives include, but are not limited to, esters, amides, aldehydes, ketones and anhydrides. Suitable CA derived esters include, but are not limited to, compounds having the general formula given by:

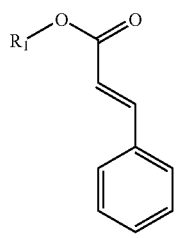

wherein R$_1$ is allyl (Takeda et al., *Tetrahedron Lett.* 36:113 (1995)), methyl (Parrish et al., *Synth. Commun.* 30:2687 (2000)), ethyl (Kumar et al., *Synth. Commun.* 14:1359 (1984)), n-butyl or other straight chain alkyl groups (Cablewski et al., WO 9959947), t-butyl (Wright et al., *Tetrahedron Lett.* 38:7345–7348 (1997)), benzyl (Ahmed et al., *Chem. Lett.* 1980, 1161), phenyl (Womack et al., *J. Org. Synth.* 111:714 (1955), hydroxyethyl (Mikhant'eva et al., *Zhumal Prikladnoi Khimii* 54:1203–1206 (1981)), vinyl (Ishihara et al., *J. Mol. Cat. B: Enzymatic* 7:307–310 (1999)), methoxyethyl (Vora et al., *Ind. Acad. Sci. Chem. Sci* 113:95–102 (2001)), or glycidyl (Nair et al., *Synth. Commun.* 29:2559–2566 1999)). The references given in parentheses, all of which are incorporated herein by reference, describe methods that may be used to synthesize the cited derivative. CA derived amides include, but are not limited to, compounds having the general formula given by:

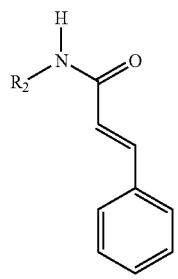

wherein R$_2$ is H (Pellegata et al., *Synthesis* 1985:517), NH$_2$ (Lifka et al., *J. fuer Praktische Chemie/Chemiker-Zeitung* 337:641–646 (1995)), benzyl (Hossain et al., *Ind. J. Chem. B* 29:1062–1063 (1990)), cyclohexyl (Ueda et al., *Bull. Chem. Soc. Jpn.* 65:1636–1641 (1992)), or phenethyl (Kunishima et al., *Tetrahedron Lett.* 40:5327–5330 (1999)). Other CA derivatives include, but are not limited to, cinnamic anhydride (Arrieta et al., *Synth. Commun.* 13:471 (1983)), cinnamaldehyde (Cha et al., *Org. Prep. Proced. Int.* 31:694–697 (1999)), the phenyl ketone of CA (Alonso et al., *J. Org. Chem.* 61:6058–6059 (1996)), the epoxide of the cinnamyl double bond (Rozen et al., *Tetrahedron Lett.* 37:531–534 (1996)), reduction of cinnamate derivatives (Elamin et al., *Tetrahedron Lett.* 29:5599 (1988)) and esters of poly(vinyl alcohol) (Chetri et al., *J. Polym. Sci. Pol. Chem.* 34:1613–1615 (1996)). The references cited in parentheses, all of which are incorporated herein by reference, describe methods that may be used to synthesize the cited derivative.

Suitable pHCA derivatives include those formed by chemical modification of the hydroxyl group, the carboxylate group or the cinnamyl double bond. Chemical derivatives formed by the modification of the carboxylate group or double bond include, but are not limited to, the same derivatives that are described for CA, supra. Derivatives of the pHCA hydroxyl group include, but are not limited to, compounds having the general formula given by:

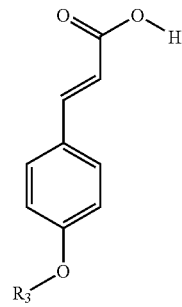

wherein R$_3$ is acetoxy (Hosoda et al., *J. Org. Chem.* 66:7199–7201 (2001)), sulfonic acid (Alexandratos et al., U.S. Pat. No. 5,990,336)), a long chain alkyl (Watanabe et al., *J. Med. Chem.* 23:50–59 (1980)), ethoxycarbonyl (Kellard et al., *Colloque Scientifique International sur le café* 12:254–259 (1988)), trimethylsilyl (Ford et al., *J. Chromatogr.* 436:484–489 (1988)), t-butyldimethylsilyl, diethyl phosphonate, or phosphate (Szardenings et al., *Tetrahedron Lett.* 37:3635–3638 (1996)). Additionally, the derivative may be a dibenzyl derivative wherein R$_3$ is benzyl and the carboxylate hydrogen is replaced with a benzyl group (Waid et al., *Tetrahedron Lett.* 37:4091–4094 (1996)) or a glycidyl ether derivative wherein R$_3$ is glycidyl and the carboxylate hydrogen is replaced with a methyl group (Erhardt et al., *J. Med. Chem.* 25:1408–1412 (1982)). The pHCA product may also be decarboxylated to pHS using the method described by Cohen et al. (*J. Amer. Chem. Soc.* 82:1907–1911 (1960)). The references cited in parentheses, all of which are incorporated herein by reference, describe methods that may be used to synthesize the cited derivative.

Suitable derivatives of pHS include, but are not limited to, various ethers and esters. Examples of ethers and esters derived from pHS include, but are not limited to, compounds having the general formula given by:

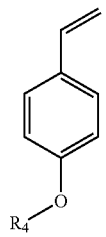

wherein $R_4$ is methyl (Hattori et al., *J. Amer. Chem. Soc.* 81:4424–4427 (1959)), t-butyl (Gable et al., *J. Amer. Chem. Soc.* 124:3970–3979 (2002)), alkyl (Hassanein et al., *J. Org. Chem.* 54:3106–3113 (1989)), silyl ethers (Nakahama et al., *Prog. Polym. Sci.* 15:299–335 (1990)), allyl (Woods et al., U.S. Pat. No. 5,633,411), t-butoxy carbonyl (Nader et al., U.S. Pat. No. 5,082,965), hydroxyethoxy (Inokuma et al., *Heterocycles* 40:401–411 (1995)), acetoxy (Sounik et al., U.S. Pat. No. 5,463,108), formate (Tessier et al., *Materials for Microlithography: Radiation-Sensitive Polymers*, ACS Symposium Series 266, American Chemical Society, Washington, D.C., 1984), glycidyl (Ericsson et al., U.S. Pat. No. 6,255,385), benzoate (Hattori et al., *J. Amer. Chem. Soc.* 81:4424–4427 (1959)), phenylcarbonate (Whitcombe et al., *J. Amer. Chem. Soc.* 117:7105–7111)), tetrahydropyran (Menzler et al., *Bioorg. Med. Chem. Lett.* 10:345–348 (2000)), benzyl (Kotecha et al., *Synlett.* 1992:395), or poly (ethylene oxide) (Inokuma et al., *Heterocycles* 54:123–130 (2001)). The references cited in parentheses, all of which are incorporated herein by reference, describe methods that may be used to synthesize the cited derivative. Additionally, pHS may be polymerized to poly(para-hydroxystyrene) and other copolymers using the methods described by Kaneko et al. in U.S. Pat. Nos. 5,959,051 and 6,258,901, both of which are incorporated herein by reference. The preferred pHS derivative of the instant invention is para-acetoxystyrene, which may be prepared using the method described by Sounik et al. in U.S. Pat. No. 5,463,108. Following derivatization, the derivatized product is recovered from the organic solvent using the methods described supra.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various uses and conditions.

Unless otherwise specified, all chemicals used in the following Examples were reagent grade and were obtained from Sigma-Aldrich (St. Louis, Mo.).

The meaning of abbreviations used is as follows: "min" means minute(s), "h" means hour(s), "rpm" means revolutions per minute, "μL" means microliter(s), "mL" means milliliter(s), "L" means liter(s), "nm" means nanometer(s), "mm" means millimeter(s), "cm" means centimeter(s), "μm" means micrometer(s), "mM" means millimolar, "M" means molar, "mmol" means millimole(s), "μmole" means micromole(s), "g" means gram(s), "μg" means microgram(s), "mg" means milligram(s), "g" means the gravitation constant, "OD" means optical density, "OD550" means the optical density at a wavelength of 550 nm, "OD600" means the optical density at a wavelength of 600 nm, "HPLC" means high performance liquid chromatography, "Aq" means aqueous phase, "Org" means organic phase, "IPTG" means isopropyl β-D-thiogalactopyranoside, and "SLPM" means standard liter per minute, "kV" means kilovolt(s), and "μF" means microfarad(s).

General Methods:

HPLC Determination of Tyrosine, Phenylalanine, CA, PHCA, and DHS:

Samples were analyzed for tyrosine, phenylalanine, CA, pHCA, and pHS using reverse-phase chromatography with an Agilent HP1100 HPLC system equipped with an autosampler, diode-array detector, and ChemStation for data acquisition and processing (Agilent Technologies, Inc., Wilmington, Del.). The analyses were done using a 4.6 mm×15 cm Zorbax SB-C18 column (3.5 μm particle size), obtained from Agilent Technologies, Inc., thermostated at 35° C. The samples were run using a flow rate of 1.0 mL/min with an eight-minute solvent gradient from 5% acetonitrile/water, containing 0.1% trifluoroacetic acid, to 80% acetonitrile/water, containing 0.1% trifluoroacetic acid. A diode-array detector set at 210, 260, and 280 nm was used to detect the various compounds at their optimum absorbance wavelength.

The aqueous samples were diluted 1:3 with water, while the organic samples were diluted 1:3 with acetonitrile before injection of 50 μL of the sample into the HPLC. A standard mixture of the analytes was prepared by mixing equal portions of solutions of the individual components, each at a concentration of 1 mg/mL.

Example 1

The Effect of DHCA and pHS on the Growth of *E. coli*

The purpose of this Example was to determine the toxicity of pHCA and pHS toward *E. coli*.

This study was done using *E. coli* TY1 (DGL430), a tyrosine overproducing strain obtained from OmniGene Bioproducts, Inc. (Cambridge, Mass.). This strain also produces phenylalanine. The seed culture of this strain was propagated in a medium consisting of $MgSO_4 \cdot 7H_2O$ (0.5 g/L), $(NH_4)_2SO_4$ (4 g/L), MOPS (20.9 g/L) and 10 mL of phosphate solution. The pH of the seed medium was adjusted to pH 6.8 and then the medium was steam-sterilized. The phosphate solution contained $KH_2PO_4$ (57.3 g/L) and $K_2HPO_4$ (110.2 g/L) and was adjusted to pH 6.8. The following solutions were then aseptically added to the seed medium to give the final concentration given in parentheses: thiamine (1 mg/L), glucose (1 g/L), lactose (15 g/L), 5 mL of a trace element solution, and tetracycline (5 mg/L). The trace element solution contained citric acid (10 g/L), $CaCl_2 \cdot 2H_2O$ (1.5 g/L), $FeSO_4 \cdot 7H_2O$ (5 g/L), $ZnSO_4 \cdot 7H_2O$ (0.39 g/L) and $CuSO_4 \cdot 5H_2O$ (0.38 g/L). The seed medium was inoculated from a frozen pre-seed culture and was grown in 250 mL baffled flasks in an Innova 4000 incubator shaker (New Brunswick Scientific Co., Edison, N.J.), incubated at 35° C. and 300 rpm for 12–16 h. One milliliter of this seed culture was used to inoculate each of the test cultures.

The test medium was 50 mL of an aqueous solution containing: $(NH_4)_2SO_4$ (4 g), 1 mL of phosphate solution, $MgSO_4 \cdot 7H_2O$ (0.5 g), and MOPS (20.9 g), with the pH adjusted to 7.0. After sterilization of this medium, thiamine (1 mg/L), 5 mL of trace element solution, glucose (2 g/L), lactose (15 g/L), IPTG (0.5 mM), and tetracycline (10 mg/L) were aseptically added to give the final concentration given in parentheses. Sodium pHCA was added to the culture flasks as shown in Table 1. The 250 mL baffled flasks containing 50 mL of the test medium were inoculated with the seed culture and were incubated at 35° C. and 300 rpm for 42 h in the incubator shaker. Samples of the culture were taken at various times and the optical density at 550 nm (OD550) was measured spectrophotometrically. The pH of these samples was also measured. After completion of the fermentation, the tyrosine and phenylalanine concentrations in the culture were measured using HPLC, as described supra. As can be seen from the results given in Table 1, pHCA inhibited cell growth when present at a concentration of 1 g/L and complete inhibition of growth was observed at a pHCA concentration of 8 g/L.

TABLE 1

The Effect of pHCA on Growth and Fermentation of E. coli

| pHCA added, g/L | 0 h OD 550 | 17.5 h OD 550 | 17.5 h pH | 29 h OD 550 | 29 h pH | 42 h OD 550 | 42 h pH | Tyr mg/L | Phe mg/L |
|---|---|---|---|---|---|---|---|---|---|
| 0.00 | ~0.05 | 1.14 | 6.75 | 5.44 | 6.13 | 5.52 | 6.17 | 700 | 200 |
| 1.00 | ~0.05 | 2.41 | 5.87 | 3.57 | 5.30 | 3.48 | 5.23 | 190 | 155 |
| 2.00 | ~0.05 | 1.27 | 5.97 | 1.47 | 5.68 | 1.53 | 5.58 | 105 | 95 |
| 4.00 | ~0.05 | 0.20 | 6.79 | 1.21 | 6.52 | 1.54 | 6.10 | 65 | 15 |
| 8.00 | ~0.05 | 0.15 | 6.84 | 0.16 | 6.82 | 0.18 | 6.79 | 15 | 10 |
| 16.00 | ~0.05 | 0.19 | 6.98 | 0.21 | 6.99 | 0.23 | 7.01 | 0 | 5 |
| 0.00 | ~0.05 | 1.19 | 6.65 | 6.49 | 6.15 | 5.20 | 6.17 | 680 | 200 |
| 1.00 | ~0.05 | 2.47 | 5.89 | 3.22 | 5.36 | 3.37 | 5.23 | 210 | 150 |
| 2.00 | ~0.05 | 1.49 | 5.89 | 1.77 | 5.64 | 1.62 | 5.54 | 100 | 95 |
| 4.00 | ~0.05 | 0.22 | 6.81 | 1.61 | 6.43 | 1.55 | 6.03 | 75 | 20 |
| 8.00 | ~0.05 | 0.15 | 6.84 | 0.16 | 6.81 | 0.17 | 6.78 | 25 | 10 |
| 16.00 | ~0.05 | 0.13 | 6.97 | 0.13 | 7.00 | 0.14 | 7.00 | 0 | 5 |

This experiment was repeated using pHS in place of pHCA. Concentrations of pHS of 0.2 g/L inhibited the growth of E. coli and no growth was observed at a concentration of 0.4 g/L. These results demonstrate that both pHCA and pHS inhibit the growth of E. coli, thereby limiting the yield of these products.

Example 2

Effect of Organic Solvents on the Growth of E. coli

The purpose of this Example was to investigate the effect of the organic solvents 1-undecanol and 2-undecanone on the growth of E. coli.

E. coli strain BNT511 was used in this study. This strain is a tyrosine overproducing strain derived from E. coli strain NST 74 (ATCC No. 31884), which was obtained from the American Type Culture Collection (ATCC) (Manassas, Va.). Strain BNT511 is deposited with the American Type Culture Collection under the terms of the Budapest Treaty on the International Recognition of the Deposit of Microorganisms for the Purposes of Patent Procedure and has been assigned a depository designation of PTA-4314. E. coli strain BNT511 was obtained as follows. A culture of E. coli strain NST 74 was grown overnight at 37° C. in three milliliters of M9 medium, prepared as follows. A solution of M9 salts buffer consisting of $KH_2PO_4$ (3 g/L), $Na_2HPO_4$ (6 g/L), NaCl (0.5 g/L), and $NH_4Cl$ (1 g/L), was prepared and the pH was adjusted to 7.4. This M9 salts buffer was autoclaved and then the following solutions, each sterilized separately by filtration (glucose) or autoclaving, were added to give the concentrations given in parentheses $MgSO_4$ (0.24 g/L), glucose (0.2%), $CaCl_2$ (0.011 g/L), and yeast extract (1 g/L). After growth, the culture was diluted by a factor of $10^3$ to $10^6$ in M9 salts buffer. Then, 100 μL of each dilution was plated on M9+1% glucose agar containing 0, 50, 150, or 450 mg/mL of 3-fluorotyrosine and the plates were incubated at 37° C. After 18 h, growth was observed only on the plate not containing 3-fluorotyrosine. Plates containing 3-fluorotyrosine were incubated an additional 24 h, after which time, several isolates were identified. One NST 74-derived isolate was obtained from each of the 150 and 450 mg/mL 3-fluorotyrosine plates. Individual isolates were propagated on M9+1% glucose agar containing 0, 50, 150, or 250 mg/mL 3-fluorotyrosine. One of these two isolates was designated as BNT511.

E. coli strain BNT511 was grown in a medium containing $KH_2PO_4$ (0.15 g/L), $Na_2HPO_4$ (0.35 g/L), $(NH_4)_2 SO_4$ (3 g/L), $MgSO_4 \cdot 7H_2O$ (0.3 g/L), yeast extract (0.5 g/L), MOPS (15.6 g/L), and glucose (10 g/L), adjusted to pH 6.8. A seed culture, taken from an active culture that grew in a fermentor and was diluted to 0.3 OD at 550 nm, was used to inoculate 30 mL of culture medium in 250 mL baffled flasks. Ten milliliters of the solvent to be tested, either 1-undecanol (98%, obtained from Aldrich) or 2-undecanone (98%, obtained from Aldrich), was added to the flask and the flasks were incubated at 35° C. and 300 rpm for 22 h in an incubator shaker. A flask without an organic solvent added served as the control. This experiment was run in duplicate. Samples of the aqueous culture media were removed at various times and the pH and the OD550 were measured. As shown by the results given in Table 2, the presence of the organic solvents tested had no significant effect on the growth of E. coli. However, the results obtained with 2-undecanone in these studies were not consistent. Specifically, 2-undecanone from some suppliers and even from different lots from the same supplier were found to inhibit growth. We believe that this variability was caused by variations in the purity of this solvent.

TABLE 2

Effect of Organic Solvents on the Growth of E. coli

| Time, h | Control, no solvent | | | | With 1-undecanol | | | | With 2-undecanone | | | |
| --- | --- | --- | --- | --- | --- | --- | --- | --- | --- | --- | --- | --- |
| | OD550 | pH | OD550 | pH | OD550 | pH | OD550 | pH | OD550 | pH | OD550 | pH |
| 0 | 0.3 | 6.8 | 0.3 | 6.8 | 0.3 | 6.8 | 0.3 | 6.8 | 0.3 | 6.8 | nt[1] | 6.8 |
| 2 | 1.012 | 7.06 | 0.96 | nt | 1.428 | 7.12 | 1.456 | nt | 1.004 | 7.3 | 1.004 | nt |
| 4.2 | 1.78 | 6.83 | 1.82 | 6.77 | 1.96 | 6.76 | 2.14 | 6.75 | 1.88 | 6.7 | 1.88 | 6.7 |
| 6 | 6.48 | nt | 6.68 | nt | 6.02 | nt | 6.7 | nt | 6.28 | nt | 6.3 | nt |
| 22 | 14.1 | 6.64 | 13.6 | 6.65 | 19.1 | 6.71 | 15.7 | 6.7 | 12.3 | 6.61 | 15.2 | 6.6 |

[1] nt means not tested

Example 3

Production of DHS in a Two-Phase Extractive Fermentation System

The purpose of this Example was to demonstrate the production of pHS in a two-phase extractive fermentation system and to compare the yield with that obtained in a single phase fermentation.

The strain used in this study was E. coli WWQ51.1, which was designed for the production of pHCA and pHS from glucose, as described in co pending U.S. Patent Application Publication No. 2004-001860. This strain also produces CA, phenylalanine, and tyrosine, and was derived by transforming E. coli NST 74 with the phenylalanine ammonia lyase gene (pal) from Rhodosporidium glutinis and the para-hydroxycinnamic acid decarboxylase gene (pdc1) from Lactobacillus plantarum.

Construction of E. coli WWQ51.1

The pdc1 gene (GenBank Accession No. U63827), given as SEQ ID NO:1, was amplified by PCR using genomic DNA from Lactobacillus plantarum as template. The genomic DNA was isolated from Lactobacillus plantarum (ATCC No. 14917) grown on MRS medium (ATCC Medium No. 416) using a DNeasy Kit (Qiagen, Valencia, Calif.). The oligonucleotide primers used to amplify the pdc1 gene were 5'-GGTAATTCATATGACAAA-3', given as SEQ ID NO:2, and 5'-TCACGTGAAACATTACTTATT-3', given as SEQ ID NO:3, which included an NdeI site (underlined nucleotides). The expected 550-bp DNA fragment was purified using a Qiagen PCR Clean Up Kit and was ligated into the pCR11-TOPO cloning vector using the TA Cloning® Kit from Invitrogen (Carlsbad, Calif.). Subsequently, this plasmid was digested with BamHI and XbaI and the fragments containing the pdc1 gene were ligated into pKSM715 (obtained from ATCC), which had been previously digested with BamHI and XbaI, to form pKSM-pdc1.

The Rhodotorula glutinis (ATCC No. 10788) pal gene, SEQ ID NO:4 (GenBank Accession No. M18261), was amplified from reverse-transcribed RNA that was purified from exponential phase cells grown in YM broth (ATCC Medium No. 200), supplemented with phenylalanine. The Rhodotorula glutinis mRNA was reversed transcribed according to the Perkin Elmer (Norwich, Conn.) GeneAmp Kit instructions without diethylpyrocarbonate (DEPC) treated water. The primers used were the random hexamers supplied with the kit. Primers used to amplify the pal gene included the upstream primer 5'-ATAGTAGMTTCATG-GCACCCTCGCTCGACTCGA-3' (SEQ ID NO:5) containing an EcoRI restriction site, and a downstream PCR primer 5'-GAGAGACTGCAGAGAGGCAGCCMGAACG-3' (SEQ ID NO:6) containing a PstI restriction site which were synthesized based on the Rhodosporidium toruloides pal gene. PCR fragments were digested with EcoRI and PstI and ligated to pKK223-3 (Amersham Biosciences, Piscataway, N.Y.), previously cut with EcoRI and PstI, forming pCA16.

Electro-competent E. coli strain NST 74 cells were prepared as follows. Samples of glycerol stocks of E. coli strain NST 74 were spread onto LB agar plates without any antibiotics and incubated overnight at 37° C. A single colony was picked, inoculated into 4.0 mL of LB medium (ATCC Medium No. 1065) and grown overnight at 37° C. One liter of LB medium was inoculated with a 1/100 volume of the fresh overnight culture. The cells were grown at 37° C., with vigorous shaking, to an OD of approximately 0.5 to 0.7 at 600 nm. The cells were centrifuged in cold centrifuge bottles in a cold rotor at 4000×g for 15 min. The supernatants were discarded and the cell pellets were gently resuspended in a total of 1.0 L of ice-cold 10% glycerol. The cells were centrifuged as described above and then resuspended in 0.5 L of ice-cold 10% glycerol. The above procedures were repeated to obtain the cells, which were resuspended in 250 mL of ice-cold 10% glycerol and washed again. The cell pellets obtained from the last washing were resuspended into a final volume of 3.0–4.0 mL in ice-cold 10% glycerol. The cell suspension was frozen in aliquots on dry ice, and stored at −80° C.

The electro-competent E. coli NST 74 cells were thawed on ice and the plasmids pKSM-pdc1 and pCA16 (~50 ng each), described above, were added to the tubes containing the cells. The DNA/cell suspensions were then transferred to pre-chilled electroporation cuvettes (0.1 cm, Bio-Rad, Hercules, Calif.) and the cuvettes were kept on ice. Each sample was electrically pulsed at 18 kV/cm in a Gene Pulser (Bio-Rad) (25 µF, 200 ohm). SOC medium (1.0 mL, available from Invitrogen) was added to each cuvette immediately after pulsing. The cell mixtures were then transferred to tubes and left on the shaker (1.0 h at 37° C., and shaken at 220 rpm). Samples (100 µL) of each transformation reaction were then pipetted onto separate LB plates, containing 100 µg/mL ampicillin and 50 µg/mL kanamycin, and incubated overnight at 37° C. Single colonies were selected and grown in LB medium containing the antibiotics overnight to give the seed culture.

Production of DHS

The seed culture was propagated in 250 mL baffled flasks, incubated at 35° C. and 300 rpm in an incubator shaker, in a medium consisting of $MgSO_4.7H_2O$ (0.5 g/L), $(NH_4)_2SO_4$ (4 g/L), MOPS (20.9 g/L) and 10 mL of phosphate solution (as described in Example 1). The pH of the seed medium was adjusted to pH 6.8 and it was steam-sterilized. The following solutions were then aseptically added to the seed medium to give the final concentration given in parentheses: thiamine (1 mg/L), glucose (15 g/L), 5 mL of a trace element solution (as described in Example 1), kanamycin (50 mg/L) and ampicillin (100 mg/L).

The seed medium was inoculated from a frozen pre-seed culture and was grown in a flask for 12–16 h. One milliliter of this seed culture was used to inoculate each of the test cultures. The test medium was 50 mL of an aqueous solution containing $(NH_4)_2SO_4$ (4 g), 1 mL of phosphate solution (as described in Example 1), $MgSO_4.7H_2O$ (0.5 g) MOPS (20.9 g) with the pH adjusted to 7.0. After sterilization of this medium, thiamine (1 mg/L), 5 mL of trace element solution (as described in Example 1), glucose (15 g/L), IPTG (0.5 mM), kanamycin (50 mg/L) and ampicillin (100 mg/L) were aseptically added to give the final concentration given in parentheses. Four test cultures were inoculated; two contained 20 mL of 2-undecanone, the other two contained no organic solvent and served as controls. The cultures were incubated in 250 mL baffled flasks in an incubator shaker at 35° C. and 300 rpm.

A sample of the aqueous phase was withdrawn at various times and the OD550, the pH, the glucose concentration, and the pHS concentration were measured. The organic phase was also sampled and the concentration of pHS was determined. The pHS concentrations were determined using HPLC, as described supra. The glucose concentration was measured either using a YSI Glucose Analyzer (YSI Inc., Yellow Springs, Ohio) or using a glucose assay kit obtained from Sigma Chemical Co. (St Louis, Mo.).

As can be seen from the results shown in Table 3, most of the pHS produced was extracted into the organic phase and the pHS production (total mg) in the two-phase system was approximately 2.5-fold higher than that obtained in the conventional single phase system.

TABLE 3

Comparison of the Production of pHS in Two-Phase and Single Phase Fermentations

| Flask No. | OD550 | Glucose g/L | pHS Aq mg/L | pHS Org mg/L |
|---|---|---|---|---|
| 0 h results | | | | |
| 1 - 1 phase | 0.12 | 17.5 | 0.009 | na[2] |
| 2 - 1 phase | 0.12 | 17.7 | 0.009 | na |
| 3 - 2 phase | 0.12 | 17.6 | nt[1] | nt |
| 4 - 2 phase | 0.12 | 17.6 | nt | nt |
| 9 h results | | | | |
| 1 - 1 phase | 6.8 | 11.4 | 3.76 | na |
| 2 - 1 phase | 7.2 | 12.4 | 2.59 | na |
| 3 - 2 phase | nt | nt | nt | nt |
| 4 - 2 phase | nt | nt | nt | nt |

TABLE 3-continued

Comparison of the Production of pHS in Two-Phase and Single Phase Fermentations

| | | | | |
|---|---|---|---|---|
| 25 h results | | | | |
| 1 - 1 phase | 10.2 | 4.73 | 15.29 | na |
| 2 - 1 phase | 9.9 | 4.53 | 9.88 | na |
| 3 - 2 phase | 9.5 | 5.38 | 0.85 | 61.65 |
| 4 - 2 phase | 10 | 4.96 | 0.89 | 79.06 |
| 50 h results | | | | |
| 1 - 1 phase | nt | 4.97 | 15.06 | na |
| 2 - 1 phase | nt | 4.57 | 16.00 | na |
| 3 - 2 phase | nt | 0.00 | 0.28 | 102.59 |
| 4 - 2 phase | nt | 0.01 | 0.28 | 96.24 |

| Summary | | | | |
|---|---|---|---|---|
| Flask No. | glucose utilization, g | pHS total mg | — | — |
| 1 - 1 phase | 0.63 | 15.06 | — | — |
| 2 - 1 phase | 0.65 | 16.00 | — | — |
| 3 - 2 phase | 0.88 | 41.32 | — | — |
| 4 - 2 phase | 0.88 | 38.78 | — | — |

[1]nt means not tested
[2]na means not applicable

Example 4

Production of pHS in a Two-Phase Extractive Fermentation System Using 1-Undecanol as Solvent The purpose of this Example was to demonstrate the production of pHS in a two-phase extractive fermentation system using 1-undecanol as solvent.

The strain used in this study was *E. coli* WWQ51.1, as described in Example 3. The seed medium used was the same as that described in Example 3. The test medium was the same as that described in Example 3, except that lactose was substituted for glucose and IPTG was added as shown in Table 4. Aliquots of the test medium (50 mL) were inoculated with a seed culture, 20 mL of 1-undecanol was added to each flask, and the cultures were incubated at 35° C. and 180 rpm for 48 h in an incubator shaker. Cultures without 1-undecanol served as controls. After this time, both the aqueous and the organic phases were sampled and analyzed for pHS using HPLC, as described supra. The results are given in Table 4.

TABLE 4

Results of the Two-Phase Extractive Fermentation of pHS Using 1-Undecanol as Solvent

| Medium mL | IPTG mM | 1-undecanol mL | pHS Aq mg/L | pHS Org mg/L | pHS/flask mg |
|---|---|---|---|---|---|
| 50 | 0 | 20 | 16 | 1425 | 29 |
| 50 | 2.5 | 20 | 15 | 1626 | 33 |
| 50 | 5 | 20 | 10 | 768 | 16 |
| 50 | 0 | 0 | 500 | na | 25 |
| 50 | 2.5 | 0 | 538 | na | 27 |
| 50 | 5 | 0 | 490 | na | 20 |

These results demonstrate that the pHS produced was extracted into the 1-undecanol organic phase and that the addition of IPTG had no significant effect on the pHS yield.

Example 5

Comparison of Organic Solvents in the Two-Phase Extractive Fermentation of pHS The purpose of this Example was to compare the organic solvents DBE obtained from E. I. Du Pont de Nemours and Co. (Wilmington, Del.), 2-undecanone, and 1-undecanol in the extractive fermentation of pHS.

The strain used in this study was *E. coli* WWQ51.1, as described in Example 3. The seed medium used was the same as that described in Example 3. The test medium used was the same as that described in Example 3, except that the glucose concentration was lowered to 10 g/L. Aliquots of the test medium (50 mL) were inoculated with a seed culture, 20 mL of the solvent to be tested was added to the appropriate flask, and the cultures were incubated at 35° C. and 300 rpm for 15 h in an incubator shaker. After this time, both the aqueous and the organic phases were sampled. The OD550, pH, glucose concentration and the pHS concentration of the aqueous phases were measured as described in Example 3. The organic phases were analyzed for pHS using HPLC, as described supra. The results are given in Table 5.

The pre-seed culture was *E. coli* strain WWQ51.1, as described in Example 3, frozen in glycerol. This culture was used to inoculate 500 mL of the seed medium consisting of $KH_2PO_4$ (0.15 g/L), $Na_2HPO_4$ (0.35 g/L), $(NH_4)_2SO_4$ (3 g/L), $MgSO_4 \cdot 7H_2O$ (0.3 g/L), yeast extract (0.5 g/L), and MOPS (15.7 g/L). The medium was adjusted to pH 6.8 and steam sterilized. Then, glucose (10 g/L), kanamycin (50 mg/L) and ampicillin (100 mg/L) were aseptically added to give the final concentration given in parentheses. The seed culture was inoculated and grown in a 2 L flask incubated at 35° C. and 300 rpm for 12 h in an incubator shaker.

The fermentor medium consisted of: 6.2 L of $H_2O$, 1.4 g $KH_2PO_4$, 3.5 g $MgSO_4 \cdot 7H_2O$, 7 g $(NH_4)_2SO_4$, 7 mL of Mazu DF204 Defoamer, obtained from BASF Corp. (Mt. Olive, N.J.), 7 mg thiamine, and 3 L of 2-undecanone, obtained from Bedoukian Research, Inc. (Danbury, Conn.). After sterilization of the medium, 250 g of a 50% w/v glucose solution and 140 mL of the trace element solution (as described in Example 1), were aseptically added. The pH of the medium was adjusted to 6.5. The final total volume of the fermentation medium was 10 L.

The seed culture was used to inoculate the fermentor medium in a 14 L Braun Fermentor, Biostat C. B. (Braun

TABLE 5

Results of the Two-Phase Extractive Fermentations of pHS Using Various Solvents

| DBE mL | 2-undecanone, mL | 1-undecanol, mL | OD 550 | Glucose g/L | pH | pHS Aq mg/L | pHS Org mg/L | Total pHS mg/L | pHS Partition coeff |
|---|---|---|---|---|---|---|---|---|---|
| 20 | 0 | 0 | 7.74 | 0.000 | 6.52 | 5 | 140 | 61 | 30 |
| 20 | 0 | 0 | 10.48 | 0.010 | 6.49 | 5 | 145 | 63 | 31 |
| 20 | 0 | 0 | 8.61 | 0.006 | 6.5 | 5 | 138 | 60 | 29 |
| 20 | 0 | 0 | 7.51 | 0.010 | 6.54 | 5 | 140 | 61 | 30 |
| 0 | 20 | 0 | 9.39 | 0.009 | 6.57 | 7 | 140 | 63 | 20 |
| 0 | 20 | 0 | 9.76 | 0.007 | 6.59 | 6 | 134 | 60 | 23 |
| 0 | 0 | 20 | 13.15 | 1.980 | 6.5 | 26 | 58 | 49 | 2 |
| 0 | 0 | 20 | 12.53 | 1.120 | 6.59 | 15 | 81 | 48 | 5 |

These results demonstrate that pHS was extracted into all three of the organic solvents tested. However, the partition coefficient for the extraction of pHS into 1-undecanol was lower than that for the other two solvents. Consequently, the amount of pHS extracted into the organic phase was higher with DBE and 2-undecanone than with 1-undecanol. Similarly, the total amount of pHS produced was higher with DBE and 2-undecanone as solvents.

Example 6

Production of pHS Using Two-Phase Extractive Fermentation in a 10 L Fermentor The purpose of this Example was to demonstrate the production of pHS using two-phase extractive fermentation in a 10 L fermentor with 2-undecanone as solvent.

Biotech International, Melesungen, Germany). The fermentation conditions were as follows: temperature: 35° C., stir rate: 400–600 rpm, airflow: 2–16 SLPM, $DO_2$: 25%, and pressure: 1 bar. Glucose was fed into the fermentor starting at a rate of 0.28 g/min. This rate was reduced when the glucose concentration rose above 2 g/L. IPTG (8 mL of a 0.5 M solution) was added when the glucose concentration fell below 4 g/L.

Samples of the aqueous and organic phases were collected at various times. The glucose, pHCA, CA, phenylalanine, tyrosine, and pHS concentrations, and the OD550 in the aqueous phase were determined, as described supra. The pHS concentration in the organic phase was measured using HPLC, as described supra. The results are shown in Table 6.

TABLE 6

The Kinetics of Cell Growth and Fermentation of Glucose to pHCA, CA, Phenylalanine, Tyrosine, and pHS in a Two-Phase Fermentation

| Time, h | OD550 | Glucose, g/L | pHCA, g/L | CA, g/L | Phe, g/L | Tyr, g/L | pHS Aq, g/L | pHS Org, g/L | Partition coeff. |
|---|---|---|---|---|---|---|---|---|---|
| 3.3 | 3.26 | 16.1 | 0.00 | 0.00 | 0.02 | 0.00 | nt[1] | nt | nt |
| 6.8 | 7.25 | 14.2 | 0.00 | 0.01 | 0.10 | 0.01 | nt | nt | nt |
| 8.6 | 10.9 | 8.8 | 0.00 | 0.01 | 0.45 | 0.05 | nt | nt | nt |
| 11.1 | 14.9 | 4.9 | 0.00 | 0.01 | 0.59 | 0.08 | nt | nt | nt |
| 13.5 | 15.4 | 1.9 | 0.00 | 0.06 | 1.12 | 0.17 | 0.004 | 0.077 | 19 |
| 15.9 | 18 | 0.5 | 0.00 | 0.18 | 1.40 | 0.28 | 0.007 | 0.095 | 14 |
| 18.3 | 20.2 | 0.0 | 0.00 | 0.35 | 1.15 | 0.29 | 0.012 | 0.239 | 19 |
| 20.2 | 20.2 | 0.0 | 0.00 | 0.50 | 1.49 | 0.37 | 0.014 | 0.365 | 27 |
| 23.3 | 21.8 | 0.0 | 0.00 | 0.70 | 1.19 | 0.37 | 0.012 | 0.411 | 33 |
| 25.5 | 21.8 | 0.0 | 0.01 | 0.85 | 1.31 | 0.42 | 0.012 | 0.559 | 45 |
| 27.3 | 22.6 | 0.0 | 0.01 | 0.80 | 1.32 | 0.45 | 0.016 | 0.665 | 40 |
| 33.6 | 18 | 0.0 | 0.01 | 1.14 | 1.13 | 0.47 | 0.045 | 0.868 | 19 |
| 36.8 | 18 | 0.1 | 0.01 | 1.16 | 1.11 | 0.48 | 0.055 | 1.030 | 19 |
| 39.3 | 20.8 | 0.0 | 0.01 | 1.19 | 1.23 | 0.52 | 0.055 | 1.164 | 21 |
| 57.1 | 18.3 | 5.5 | 0.01 | 1.57 | 0.82 | 0.44 | 0.090 | 1.570 | 17 |
| 59.4 | 18.1 | 7.5 | 0.01 | 1.58 | 0.84 | 0.44 | 0.082 | 1.769 | 22 |
| 63.8 | 17 | 7.0 | 0.01 | 1.75 | 0.81 | 0.42 | 0.064 | 1.753 | 27 |

[1]nt means not tested

These results demonstrate the successful production of pHS in a two-phase extractive fermentation in a 10 L fermentor using 2-undecanone as solvent.

Example 7

Production of Cinnamic Acid (CA) in a Two-Phase Extractive Fermentation System The purpose of this example was to demonstrate the production of cinnamic acid in a two-phase extractive fermentation system. In addition, the effect of IPTG, the solvents 2-undecanone and 1-undecanol, and the addition of pHS were investigated.

The strain used in this study was *E. coli* WWQ51.1, as described in Example 3. The conditions were similar to those described in Example 3. Eight test cultures were inoculated; six contained 20 mL of 2-undecanone, the other two contained 20 mL of 1-undecanol. A 10% w/v solution of pHS in propylene glycol (0.5 mL), obtained from Sigma-Aldrich, Milwaukee, Wis., was added to two of the cultures containing 2-undecanone, as specified in Table 7.

The cultures were incubated in 250 mL baffled flasks at 35° C. and 300 rpm for 24 h in an incubator shaker. After this time, a sample of the aqueous phase was withdrawn and the pH, OD550, and the concentration of the fermentation products were measured, as described supra. The organic phase was also sampled and the concentration of CA and pHS were determined using HPLC, as described supra.

The results are given in Tables 7, 8, and 9. The data in Tables 7 and 8 demonstrates that *E. coli* can grow in the presence of an inhibitory concentration of pHS in a two-phase fermentation system with 2-undecanone as solvent. Additionally, the addition of IPTG had a significant effect on the amount of CA produced. The results obtained with 1-undecanol were similar to those obtained with 2-undecanone as solvent.

In this study, the pH decreased to low values and a significant amount of CA was extracted into both organic solvents tested. The amount of pHS produced was low, probably because of its poor stability at low pH. As shown by the data in Table 9, the amount of CA extracted into the organic phase was very dependent on the pH of the medium. This pH dependence results because the fully protonated species is the form extracted into the organic phase. The ionized acid form is very water-soluble and is not extracted into the organic phase. Therefore, the extractive fermentation of acidic compounds such as CA and pHCA is favored at low pH, where the acid exists primarily in the unionized form.

TABLE 7

Effect of Added pHS and IPTG on the Growth and Glucose Utilization of *E. coli* in Two-Phase Fermentations

| Flask No. | IPTG, mM | Solvent added | pHS (10% w/v) added | OD550 0 h | Glucose g/L, 0 h | OD550 24 h | Glucose g/L, 24 h | pH, 24 h |
|---|---|---|---|---|---|---|---|---|
| 1 | 0 | 2-Undecanone | None | 0.13 | 15.2 | 15.1 | 0.0 | 5.38 |
| 2 | 0 | 2-Undecanone | None | 0.13 | 15.2 | 12.1 | 2.7 | 4.5 |
| 3 | 0.5 | 2-Undecanone | None | 0.13 | 15.2 | 12.9 | 0.0 | 5.5 |
| 4 | 0.5 | 2-Undecanone | None | 0.13 | 15.2 | 12.3 | 0.0 | 5.4 |
| 5 | 0.5 | 2-Undecanone | 0.5 mL | 0.13 | 15.2 | 15.7 | 0.0 | 4.8 |
| 6 | 0.5 | 2-Undecanone | 0.5 mL | 0.13 | 15.2 | 12.5 | 0.0 | 5.7 |

TABLE 7-continued

Effect of Added pHS and IPTG on the Growth and Glucose Utilization of E. coli in Two-Phase Fermentations

| Flask No. | IPTG, mM | Solvent added | pHS (10% w/v) added | OD550 0 h | Glucose g/L, 0 h | OD550 24 h | Glucose g/L, 24 h | pH, 24 h |
|---|---|---|---|---|---|---|---|---|
| 7 | 0.5 | 1-Undecanol | None | 0.13 | 15.2 | 15.3 | 0.0 | 5.7 |
| 8 | 0.5 | 1-Undecanol | None | 0.13 | 15.2 | 15.3 | 0.0 | 5.71 |

TABLE 8

Concentration of Fermentation Products in Two-Phase Fermentations

| | Results in aqueous phase | | | | | Results in organic phase | | |
|---|---|---|---|---|---|---|---|---|
| Flask No. | Tyr mg/L | Phe mg/L | pHCA mg/L | CA mg/L | pHS mg/L | pHCA mg/L | CA mg/L | pHS, mg/L |
| 1 | 347 | 1087 | 3 | 11 | nd[1] | <1 | 39 | nd |
| 2 | 137 | 796 | <1 | 2 | nd | <1 | 34 | nd |
| 3 | 376 | 951 | 22 | 132 | nd | 1 | 189 | nd |
| 4 | 371 | 942 | 14 | 90 | nd | 1 | 229 | nd |
| 5 | 268 | 826 | 5 | 26 | nd | 1 | 210 | 3411 |
| 6 | 350 | 938 | 21 | 137 | nd | 1 | 151 | 3966 |
| 7 | 431 | 1008 | 16 | 84 | nd | 3 | 176 | 46 |
| 8 | 428 | 990 | 17 | 88 | nd | 3 | 189 | 33 |

[1] nd means not detected

TABLE 9

Results of the Two-Phase Extractive Fermentation of CA

| Flask No. | Solvent added 20 mL/flask | pH | CA Aq, mg/L | CA Org, mg/L | CA Org/ CA Aq |
|---|---|---|---|---|---|
| 1 | 2-undecanone | 5.38 | 11 | 39 | 3.55 |
| 2 | 2-undecanone | 4.5 | 2 | 34 | 17.00 |
| 3 | 2-undecanone | 5.5 | 132 | 189 | 1.43 |
| 4 | 2-undecanone | 5.4 | 90 | 229 | 2.54 |
| 5 | 2-undecanone | 4.8 | 26 | 210 | 8.08 |
| 6 | 2-undecanone | 5.7 | 137 | 151 | 1.10 |
| 7 | 1-undecanol | 5.7 | 84 | 176 | 2.10 |
| 8 | 1-undecanol | 5.71 | 88 | 189 | 2.15 |

Example 8

Toxicity Testing of Organic Solvents Toward E. coli

The purpose of this Example was to screen other organic solvents for toxicity toward E. coli using agar cultures.

This study was done using E. coli TY1 (DGL430), as described in Example 1. A stock culture of this strain was prepared in 50% glycerol and stored at −20° C. This stock culture (10 μL) was used to inoculate a 14 mL Falcon™ tube (BD Biosciences, Bedford, Mass.) containing 5 mL of LB medium, consisting of Bacto-tryptone (10 g/L), Bacto-yeast extract (5 g/L), and NaCL (10 g/L) adjusted to pH 7.5 with NaOH, and supplemented with tetracycline (10 μg/mL). This culture was incubated at 34° C. and 250 rpm overnight in an incubator shaker until an OD600 of between 1.0 and 2.0 was obtained. Dilutions of this culture were spread onto LB agar plates. The appropriate dilution was determined by experimentation to obtain between 100 to 200 colonies per plate. Three plates were used as controls and the remaining plates were used to test the solvents listed in Table 10. The solvents (5 mL) were filtered through a 0.2 μm filter onto the inoculated agar plates. All the solvents were tested in triplicate.

TABLE 10

Organic Solvents Used in Toxicity Testing

| Solvent Name | CAS No. | Source | Purity |
|---|---|---|---|
| Diisopentyl ether | 544-01-4 | Sigma-Aldrich | 99% |
| Methyl decanoate | 110-42-9 | Sigma-Aldrich | 99% |
| Propyl Benzoate | 2315-68-6 | Sigma-Aldrich | 99% |
| Dibenzyl ether | 103-50-4 | Sigma-Aldrich | 99% |
| 2-Decanone | 693-54-9 | Sigma-Aldrich | 99% |
| 1-Phenyl-1-pentanone | 1009-14-9 | Sigma-Aldrich | 99% |
| 2-Tridecanone | 593-08-8 | Sigma-Aldrich | 99% |
| 2-Undecanone | 112-12-9 | Sigma-Aldrich | 97+% |
| DBE | 71195-64-7 141-04-8 925-06-4 | E.I. du Pont de Nemours and Co. | 98.5% |

The plates were incubated overnight at 30° C. in a vented incubator located in a chemical fume hood. The colonies formed were counted after 24 and 48 h. The colony forming units (CFUs) obtained with each solvent were compared to those of the control plates and plotted in FIG. 1 as a percentage versus the log P value for the solvent (P values obtained from Hansch et al., Exploring QSAR: Hydrophobic, Electronic and Steric Constants, American Chemical Society, Washington, D.C., 1995). The raw data for FIG. 1 is given in Table 11. As can be seen from the data in FIG. 1 and Table 11, there is a general pattern of decreasing toxicity toward E. coli with increasing log P values. The error bars in the figure represent the range of the data. Cell growth on the agar medium was characterized by the presence of both distinct and non-distinct colony formations, which affected the precision of the colony counts. In the presence of some of the solvents tested, growth continued between 24 and 48 h, while with other solvents, no further growth was observed after 24 h. From these results, three solvents were identified as being relatively nontoxic to E. coli, 2-tridecanone, methyl decanoate, and DBE, all having a log P value above 3.7. The solvent 2-undecanone was found to significantly inhibit growth in this study, possibly due to impurities in the lot used.

TABLE 11

Raw Data for the Toxicity Testing Results Shown in FIG. 1

| Solvent | Log P | % CFU Sample 1 | % CFU 1 Sample 2 | % CFU Sample 3 |
|---|---|---|---|---|
| DBE | 3.84 | 65 | 99 | 35 |
| Methyl decanoate | 4.41 | 73 | 109 | 44 |
| 1-Phenyl-1-pentanone | 3.33 | 33 | 62 | 0 |
| 2-Decanone | 3.39 | 0 | 0 | 0 |
| Dibenzyl ether | 3.1 | 1.5 | 5 | 0 |
| 2-Tridecanone | 4.95 | 100 | 115 | 87 |
| 2-Undecanone | 3.91 | 11 | 11 | 11 |
| Propyl benzoate | 3.01 | 9 | 26 | 0.9 |
| Diisopentyl ether | 3.96 | 13 | 39 | 0 |

Example 9

The Effect of pHS on the Growth of *Pseudomonas putida*

The purpose of this Example was to determine the toxicity of pHS toward *Pseudomonas putida*.

This study was done using *P. putida* strain S12 (ATCC No. 700801), obtained from the American Type Culture Collection. This *P. putida* strain was grown at 30° C. in 20 mL of LB medium containing 0.25% glucose and 10 mM $MgSO_4$ in a 125 mL baffled flask until stationary phase was achieved. Aliquots from this stationary phase culture were plated on LB agar plates containing 0.25% glucose, 10 mM $MgSO_4$, and 1 g/L pHS, and incubated at 30° C. for several days. Colonies from these plates were streaked on identical plates and grown as described above. An individual colony from these plates was used to inoculate 20 mL of liquid LB medium containing 0.5% glucose, 10 mM $MgSO_4$ and 1 g/L pHS. This culture was grown in a 125 mL baffled flask at 30° C. and 200 rpm in an incubator shaker until stationary phase was achieved. These stationary phase cells (0.5 mL) were added to 20 mL of a test medium consisting of LB medium, 0.5% glucose, 10 mM $MgSO_4$ and either 0, 1.0, or 1.25 g/L pHS. These cultures were grown in 125 mL baffled flasks at 30° C. and 200 rpm in an incubator shaker. Cell growth in these cultures was monitored by taking aliquots, diluting them with an equal volume of 1,2-propanediol, and measuring the OD at 600 nm. These OD measurements were used to calculate the doubling time and growth rate as a percentage of growth observed in the test medium without pHS. The results from this study are given in Table 12.

TABLE 12

Growth of *P. putida* in the Presence of pHS

| pHS, g/L | Doubling Time, min | Growth Rate, % |
|---|---|---|
| 0 | 99 | 100 |
| 1.0 | 118 | 85 |
| 1.25 | 111 | 90 |

These results demonstrate that *P. putida* can be adapted to be tolerant to pHS. Comparison of these results to those given in Example 1, shows that *P. putida* is much more tolerant to pHS than *E. coli* because the growth of the *E. coli* strain tested in Example 1 was totally inhibited at a pHS concentration of 0.4 g/L

Example 10

The Effect of DHCA on the Growth of *Pseudomonas putida*

The purpose of this Example was to determine the toxicity of pHCA toward *Pseudomonas putida*.

This study was done using *P. putida* strain KT2440 (obtained from Juan Ramos at Consejo Superior de Investigaciones Cientificas, Granada, Spain and *P. putida* strain NCIMB 9866 (obtained from the National Collections of Industrial, Food and Marine Bacteria Ltd., Scotland, UK). *P. putida* strain KT2440 is also available from the American Type Culture Collection as ATCC No. 47054). Liquid cultures of these strains were grown in 10 mL of LB medium containing 0.25% glucose and 10 mM $MgSO_4$ in 50 mL screw-capped, glass tubes at 30° C. and 200 rpm in an incubator shaker. In all subsequent media, pHCA was added from a 60 g/L stock solution, which was adjusted to pH 7.0 using KOH and then filter-sterilized. Samples of each culture were streaked on LB agar plates containing 0.25% glucose, 10 mM $MgSO_4$ and 30 g/L pHCA and grown at 30° C. Individual colonies taken from these plates were grown to stationary phase at 30° C. in 10 mL of LB medium containing 0.5% glucose, 10 mM $MgSO_4$ and 25 g/L pHCA in 50 mL screw-capped, glass tubes. These stationary phase cultures were diluted 1:25 in fresh LB medium containing 0.5% glucose, 10 mM $MgSO_4$ and either 0 or 25 g/L pHCA and grown in 50 mL screw-capped, glass tubes at 30° C. and 200 rpm in an incubator shaker. Cell growth in these cultures was monitored by taking aliquots and measuring the OD at 600 nm of the culture or dilutions of the culture, which were made with LB medium. These OD measurements were used to calculate the doubling time and growth rate as a percentage of growth observed in test medium without pHCA. The results from this study are given in Table 13.

TABLE 13

Growth of *Pseudomonas putida* Strains in the Presence of pHCA

| Strain | pHCA, g/L | Doubling Time, min | Growth Rate, % |
|---|---|---|---|
| *P. putida* NCIMB 9866 | 0 | 19 | 100 |
| *P. putida* NCIMB 9866 | 25 | 105 | 18 |
| *P. putida* KT2440 | 0 | 17 | 100 |
| *P. putida* KT2440 | 25 | 79 | 21 |

These results demonstrate that *Pseudomonas putida* is more tolerant to pHCA than the *E. coli* strain tested in Example 1 (see Table 1), which was significantly inhibited at a pHCA concentration of 8 g/L.

What is claimed is:

1. A process for the production of a multifunctional aromatic compound comprising:
   (a) providing a production host which produces a multifunctional aromatic compound selected from the group consisting of cinnamic acid, para-hydroxycinnamic acid, and para-hydroxystyrene and mixtures thereof;
   (b) growing the production host in a fermentation medium wherein the production host produces a multifunctional aromatic compound into the fermentation medium to produce a conditioned medium;
   (c) mixing the fermentation medium of (b) with an extractant selected from the group consisting of diisopentyl ether, n-propyl benzoate, 2-undecanone, dibenzyl ether, 2-tridecanone, 2-decanone, 1-phenyl-1-pentanone, methyl decanoate, 1-undecanol, diisobutyl DBE-IB and mixtures thereof, for a time sufficient to allow extraction of the multifunctional aromatic compound into the extractant;
   (d) separating the extractant from the fermentation medium; and
   (e) recovering the multifunctional aromatic compound from the extractant.

2. A process according to claim 1 wherein the amount of extractant mixed with the fermentation medium of step (c) is from about 3% to about 60% by volume.

3. A process for the production of a multifunctional aromatic compound comprising:
   (a) providing a production host which produces a multifunctional aromatic compound selected from the group consisting of cinnamic acid, para-hydroxycinnamic acid, and para-hydroxystyrene and mixtures thereof;
   (b) growing the production host of step (a) in a biphasic growth medium comprising a fermentation medium containing from about 3% to about 60% by volume of an extractant, the extractant selected from the group consisting of diisopentyl ether, n-propyl benzoate, 2-undecanone, dibenzyl ether, 2-tridecanone, 2-decanone, 1-phenyl-1-pentanone, methyl decanoate, 1-undecanol, diisobutyl DBE-IB and mixtures thereof; for a time sufficient to allow extraction of the multifunctional aromatic compound into the extractant;
   (c) separating the extractant from the fermentation medium; and
   (d) recovering the multifunctional aromatic compound from the extractant.

4. A process according to claim 3 wherein after step (d) the extractant is optionally added back to the biphasic growth medium.

5. A process according to claim 3 wherein the fermentation medium after step (c) is optionally added back to the biphasic growth medium.

6. A process according to claim 1 wherein the production host is removed from the fermentation medium prior to mixing the fermentation medium with the extractant.

7. A process according to claim 6 wherein the production host is removed from the fermentation medium by filtration or centrifugation.

8. A process according to either claim 1 or claim 3 wherein the extractant is separated from the fermentation medium by use of a gravity settler, a centrifuge, or a hydrocyclone.

9. A process according to either claim 1 or claim 3 wherein nutrients are added continuously or periodically to the fermentor.

10. A process according to either claim 1 or claim 3 wherein the recovering of step 11(e) or 13(d) is accomplished by means of distillation, adsorption by resins, or separation by molecular sieves.

11. A process according to either claim 1 or claim 3 wherein the production host is selected from the group consisting of *Escherichia, Methylosinus, Methylomonas, Psuedomonas, Streptomyces, Corynebacterium*, and *Rhodobacter*.

12. A process according to claim 11 wherein the production host overproduces an amino acid selected from the group consisting of tyrosine and phenylalanine.

13. A process according to claim 11 wherein the production host is selected from the group consisting of *Escherichia* and *Pseudomonas*.

14. A process according to claim 13 wherein the production host is *Escherichia coli* or *Pseudomonas putida*.

15. A process according to either claim 1 or claim 3 wherein the production host is grown in a fermentor selected from the group consisting of a stirred tank fermentor, an airlift fermentor, and a bubble fermentor.

* * * * *

SEQUENCE LISTING

<160> NUMBER OF SEQ ID NOS: 6

<210> SEQ ID NO 1
<211> LENGTH: 535
<212> TYPE: DNA
<213> ORGANISM: Lactobacillus plantarum

<400> SEQUENCE: 1

| | | | | | |
|---|---|---|---|---|---|
| atgacaaaaa | cttttaaaac | acttgatgac | tttctcggca | cacactttat | ctacacttat | 60 |
| gataacggct | gggaatacga | gtggtacgcc | aagaacgacc | acaccgttga | ttaccgaatc | 120 |
| cacggtggga | tggttgccgg | tcgttgggtc | actgatcaaa | agctgacat | cgtcatgttg | 180 |
| accgaaggca | tttacaaaat | ttcttggact | gaaccaactg | ggactgacgt | tgcactagac | 240 |
| ttcatgccca | atgagaagaa | actacacggt | acgattttct | tcccaaagtg | ggttgaagaa | 300 |
| caccctgaaa | ttacggtcac | ttaccaaaac | gaacacatcg | atttaatgga | acagtctcgt | 360 |
| gaaaagtatg | ccacttatcc | aaaactagtt | gtacccgaat | ttgccaatat | tacttacatg | 420 |
| ggcgagggcc | aaaacaatga | agatgtaatc | agtgaagcac | cttacaaaga | aatgccgaat | 480 |
| gatattcgca | acggcaagta | cttgatcaaa | actaccatcg | tttaaataag | taatg | 535 |

<210> SEQ ID NO 2
<211> LENGTH: 18
<212> TYPE: DNA
<213> ORGANISM: artificial sequence
<220> FEATURE:
<223> OTHER INFORMATION: Primer

<400> SEQUENCE: 2
ggtaattcat atgacaaa                                                    18

<210> SEQ ID NO 3
<211> LENGTH: 21
<212> TYPE: DNA
<213> ORGANISM: artificial sequence
<220> FEATURE:
<223> OTHER INFORMATION: Primer

<400> SEQUENCE: 3
tcacgtgaaa cattacttat t                                                21

<210> SEQ ID NO 4
<211> LENGTH: 2703
<212> TYPE: DNA
<213> ORGANISM: Rhodotorula glutinis

<400> SEQUENCE: 4

| | | | | | |
|---|---|---|---|---|---|
| atggcaccct | cgctcgactc | gatctcgcac | tcgttcgcaa | acggcgtcgc | atccgcaaag | 60 |
| caggctgtca | atggcgcctc | gaccaacctc | gcagtcgcag | gctcgcacct | gccccacaac | 120 |
| ccaggtcacg | caggtcgaca | tcgtcgagaa | gatgctcgcc | gcgccgaccg | actcgacgct | 180 |
| cgaactcgac | ggctactcgc | tcaacctcgg | agacgtcgtc | tcggccgcga | ggaagggcag | 240 |
| gcctgtccgc | gtcaaggaca | gcgacgagat | ccgctcaaag | attgacaaat | cggtcgagtt | 300 |
| cttgcgctcg | cagtgagagt | cgtgctttcg | ttctctggcg | tcgagagggc | gggacctttcc | 360 |
| caagttgcca | agggactgac | tgtcgctctc | ctgtgtcgcg | cagactctcc | atgagcgtct | 420 |
| acggcgtcac | gactggatttt | ggcggatccg | cagacacccg | caccgaggac | gccatctcgc | 480 |
| tccagaaggc | gtgcgtcctc | ctcgtctccc | tctcgcttct | cgagcttcgg | actgaccgtc | 540 |

-continued

```
ttcccgcaca gtctcctcga gcaccagctc tgcggtgttc tcccttcgtc gttcgactcg      600
ttccgcctcg gccgcggtct cgagaactcg cttcccctcg aggttgttcg cggcgccatg      660
acaatccgcg tcaacagctt gacccggtga gttgccgtcc ttactcactc agcggtcttc      720
gagctgacag ttggcgcacc cagcggccac tcggctgtcc gcctcgtcgt cctcgaggcg      780
ctcaccaact tcctcaacca cggcatcacc cccatcgtcc cctccgcgg caccatctct       840 gcgtcgggcg acctctctcc tctctcctac attgcagcgg ccatcagcgg tcacccggac      900
agcaaggtgc acgtcgtcca cgagggcaag gagaagatcc tgtacgcccg cgaggcgatg      960
gcgctcttca acctcgagcc cgtcgtcctc ggcccgaagg aaggtctcgg tctcgtcaac     1020
ggcaccgccg tctcagcatc gatggccacc ctcgctctgc acgacgcaca catgctctcg     1080
ctcctctcgc agtcgctcac ggccatgacg gtcgaagcga tggtcggcca cgccggctcg     1140
ttccacccct tccttcacga cgtcacgcgc cctcacccga cgcagatcga agtcgcggga     1200
aacatccgca agctcctcga gggaagccgc tttgctgtcc accatgagga ggaggtcaag     1260
gtcaaggacg acgagggcat tctccgccag gaccgctacc ccttgcgcac gtctcctcag     1320
gtgcgcttac ttctgtttgt tctgccgaag acatgacgct gacgtccgct tactcgcgca     1380
gtggctcggc ccgctcgtca gcgacctcat tcacgcccac gccgtcctca ccatcgaggc     1440
cggccagtcg acgaccgaca accctctcat cgacgtcgag aacaagactt cgcaccacgg     1500
cggcaatttc caggctgccg ctgtggccaa caccatggag aagactcggt gcgccgcttc     1560
actgtgacct gttctcttgg tctcgtcctg acgagtacgc tgtgcagcct cgggctcgcc     1620
cagatcggca agctcaactt cacgcagctc accgagatgc tcaacgccgg catgaaccgc     1680
ggcctccccc cctgcctcgc ggccgaagac ccctcgctct cctaccactg caagggcctc     1740
gacatcgccg ctgcggcgta cacctcggag ttgggacacc tcgccaaccc tgtgacgacg     1800
catgtccagc cggctgagat ggcgaaccag gcggtcaact cgcttgcgct catctcggct     1860
cgtcgcacga ccgagtccaa cgacgtcctt tctctcgtga gtcaggcgct catcacactc     1920
gcgaacagaa gctgacgcac tcggtctcgc agctcctcgc cacccacctc tactgcgttc     1980
tccaagccat cgacttgcgc gcgatcgagt tcgagttcaa gaagcagttc ggcccagcca     2040
tcgtctcgct catcgaccag cactttggct ccgccatgac cggctcgaac ctgcgcgacg     2100
agctcgtcga aaggtgaac aagacgctcg ccaagcgcct cgagcagacc aactcgtacg     2160
acctcgtccc gcgctggcac gacgccttct ccttcgccgc cggcaccgtc gtcgaggtcc     2220
tctcgtcgac gtcgctctcg ctcgccgccg tcaacgcctg gaaggtcgcc gccgccgagt     2280
cggccatctc gctcacccgc caagtccgcg agacttctg gtccgccgcg tcgacctcgt     2340
cgcccgcgct ctcgtacctc tcgccgcgca ctcagatcct ctacgccttc gtccgcgagg     2400
agcttggcgt caaggcccgc cgcggagacg tcttcctcgg caagcaagag gtgacgatcg     2460
gctcgaacgt ctccaagatc tacgaggcca tcaagtcggg caggatcaac aacgtcctcc     2520
tcaagatgct cgcttagaca ctcttcccac tctcgcatcc cttccatacc ctatcccgcc     2580
tgcacttctt aggactcgct tcttgtcgga ctcggatctc gcatcgcttc tttcgttctt     2640
ggctgcctct ctagaccgtg tcggtattac ctcgagattg tgaatacaag cagtacccat     2700
cca                                                                   2703
```

<210> SEQ ID NO 5
<211> LENGTH: 34
<212> TYPE: DNA

-continued

```
<213> ORGANISM: artificial sequence
<220> FEATURE:
<223> OTHER INFORMATION: Primer

<400> SEQUENCE: 5
atagtagaat tcatggcacc ctcgctcgac tcga                            34

<210> SEQ ID NO 6
<211> LENGTH: 29
<212> TYPE: DNA
<213> ORGANISM: artificial sequence
<220> FEATURE:
<223> OTHER INFORMATION: Primer

<400> SEQUENCE: 6
gagagactgc agagaggcag ccaagaacg                                  29
```